US007449339B2

(12) United States Patent
Samsoondar et al.

(10) Patent No.: US 7,449,339 B2
(45) Date of Patent: *Nov. 11, 2008

(54) SPECTROSCOPIC METHOD AND APPARATUS FOR TOTAL HEMOGLOBIN MEASUREMENT

(75) Inventors: James Samsoondar, Cambridge (CA); Duncan MacIntyre, Campbellville (CA)

(73) Assignee: NIR Diagnostics Inc., Campbellville (CA)

( * ) Notice: Subject to any disclaimer, the term of this patent is extended or adjusted under 35 U.S.C. 154(b) by 924 days.

This patent is subject to a terminal disclaimer.

(21) Appl. No.: 10/845,227

(22) Filed: May 14, 2004

(65) Prior Publication Data

US 2005/0019936 A1 Jan. 27, 2005

Related U.S. Application Data

(63) Continuation-in-part of application No. 10/823,778, filed on Apr. 14, 2004, which is a continuation-in-part of application No. 10/805,290, filed on Mar. 22, 2004, now abandoned, which is a continuation of application No. 09/875,143, filed on Jun. 7, 2001, now Pat. No. 6,711,516, which is a continuation-in-part of application No. 09/773,495, filed on Feb. 2, 2001, now abandoned, which is a continuation-in-part of application No. 09/697,679, filed on Oct. 27, 2000, now abandoned, which is a continuation-in-part of application No. 09/447,215, filed on Nov. 23, 1999, now Pat. No. 6,470,279, application No. 10/845,227, which is a continuation-in-part of application No. 10/319,492, filed on Mar. 7, 2003, now Pat. No. 7,157,282, which is a continuation-in-part of application No. 10/023,869, filed on Dec. 21, 2001, now Pat. No. 6,828,152, application No. 10/845,227, which is a continuation-in-part of application No. 10/136,329, filed on May 2, 2002, now Pat. No. 6,949,384, which is a continuation-in-part of application No. 10/023,869, filed on Dec. 21, 2001, now Pat. No. 6,828,152, application No. 10/845,227, which is a continuation-in-part of application No. 10/042,258, filed on Jan. 11, 2002, now Pat. No. 6,841,132, which is a continuation-in-part of application No. 09/958,933, filed as application No. PCT/CA00/00549 on May 11, 2000, now Pat. No. 6,582,964.

(51) Int. Cl.
*G01N 33/72* (2006.01)
*G01N 21/00* (2006.01)

(52) U.S. Cl. .................. 436/66; 436/63; 436/164; 422/82.05; 422/82.09; 702/19

(58) Field of Classification Search .............. 422/82.05, 422/82.09; 436/63, 66, 67, 80, 164, 171, 436/46; 702/19
See application file for complete search history.

(56) References Cited

U.S. PATENT DOCUMENTS 3,876,377 A 4/1975 Cinqualbre
(Continued)

FOREIGN PATENT DOCUMENTS

CA 2216657 10/1996
(Continued)

OTHER PUBLICATIONS

XP002146317—*Katalog Merk, Verbrauchsmaterialien und Gerate*, see "Zylindrische Kuvetten," Merck Eurolab GMBH, Darmstadt, Germany, p. 634.9 (1999).
(Continued)

*Primary Examiner*—Maureen M Wallenhorst
(74) *Attorney, Agent, or Firm*—Arent Fox LLP

(57) ABSTRACT

A method and apparatus for measuring Tot-Hb in a sample are provided. The method involves collecting absorbance measurements of a sample using a spectroscopic apparatus that includes a first primary calibration algorithm for one of Oxy-Hb, "Oxy-Hb plus Deoxy-Hb", or "Total-Hb minus Met-Hb" and a second primary calibration algorithm for one or more than one of Met-Hb, Carboxy-Hb, or Sulf-Hb, or includes a third primary calibration algorithm obtained by adding terms of the first primary calibration algorithm and the second primary calibration algorithm together. Followed by predicting either a first value for one of Oxy-Hb, "Oxy-Hb plus Deoxy-Hb," or "Total-Hb minus Met-Hb" and predicting second value for one or more than one of Met-Hb, Carboxy-Hb, or Sulf-Hb in the sample and adding the first and second value together, or predicting a value for Total-Hb.

27 Claims, 9 Drawing Sheets

U.S. PATENT DOCUMENTS

| | | | |
|---|---|---|---|
| 4,001,142 A | 1/1977 | Turner | |
| 4,069,016 A | 1/1978 | Wu | |
| 4,116,336 A | 9/1978 | Sorensen et al. | |
| 4,134,678 A | 1/1979 | Brown et al. | |
| 4,297,143 A | 10/1981 | Kleinschmit et al. | |
| 4,387,972 A | 6/1983 | Valencia | |
| 4,535,778 A | 8/1985 | Kitrilakis et al. | |
| 4,575,240 A | 3/1986 | Hess et al. | |
| 4,603,044 A | 7/1986 | Geho et al. | |
| 4,722,598 A | 2/1988 | Ford | |
| 4,734,260 A | 3/1988 | Lautenschlager | |
| 4,772,561 A | 9/1988 | Genshaw | |
| 4,791,938 A | 12/1988 | Van Valkenburg | |
| 4,866,644 A | 9/1989 | Shenk et al. | |
| 5,004,584 A | 4/1991 | Rayman | |
| 5,134,284 A | 7/1992 | Volgyesi | |
| 5,151,369 A | 9/1992 | Lewis et al. | |
| 5,207,984 A | 5/1993 | Kheiri | |
| 5,278,073 A | 1/1994 | Grandjean | |
| 5,306,623 A | 4/1994 | Kiser et al. | |
| 5,310,679 A | 5/1994 | Artiss et al. | |
| 5,361,758 A | 11/1994 | Hall et al. | |
| 5,429,128 A | 7/1995 | Cadell et al. | |
| 5,430,542 A | 7/1995 | Shepherd | |
| 5,447,838 A | 9/1995 | Meiklejohn et al. | |
| 5,521,154 A | 5/1996 | Garlick et al. | |
| 5,637,505 A | 6/1997 | Li et al. | |
| 5,675,410 A | 10/1997 | Kanda | |
| 5,724,268 A | 3/1998 | Sodickson et al. | |
| 5,725,774 A | 3/1998 | Neyer | |
| 5,800,781 A | 9/1998 | Gavin et al. | |
| 5,812,312 A | 9/1998 | Lorincz | |
| 5,846,492 A | 12/1998 | Jacobs et al. | |
| 5,929,031 A | 7/1999 | Kerwin et al. | |
| 5,939,327 A | 8/1999 | Samsoondar | |
| 6,013,528 A | 1/2000 | Jacobs et al. | |
| 6,022,849 A | 2/2000 | Olson et al. | |
| 6,177,283 B1 | 1/2001 | Ray | |
| 6,195,158 B1 | 2/2001 | Cadell et al. | |
| 6,268,910 B1 | 7/2001 | Samsoondar et al. | |
| 6,277,584 B1 | 8/2001 | Chu et al. | |
| 6,372,503 B1 | 4/2002 | Samsoondar | |
| 6,567,214 B2 | 5/2003 | Lorincz | |
| 6,689,612 B2 * | 2/2004 | Samsoondar | 436/8 |
| 6,711,516 B2 | 3/2004 | Samsoondar | |
| 6,828,152 B2 | 12/2004 | Samsoondar | |
| 2001/0004285 A1 | 6/2001 | Cadell et al. | |
| 2002/0110496 A1 | 8/2002 | Samsoondar | |
| 2003/0027341 A1 | 2/2003 | Samsoondar | |
| 2003/0068822 A1 | 4/2003 | Jacobs et al. | |

FOREIGN PATENT DOCUMENTS

| | | |
|---|---|---|
| CA | 2169803 | 11/1996 |
| CA | 2283154 | 9/1998 |
| EP | 0 132 399 | 1/1985 |
| EP | 0 222 419 | 5/1987 |
| EP | 0 376 135 | 7/1990 |
| EP | 0 598 329 | 5/1994 |
| EP | 0 631 137 | 12/1994 |
| EP | 0 881 495 | 12/1998 |
| GB | 2385663 A | 8/2003 |
| GB | 2 390 420 | 1/2004 |
| WO | WO 87/06343 | 10/1987 |
| WO | WO 94/08225 | 4/1994 |
| WO | WO 97/19340 | 5/1997 |
| WO | WO 97/47972 | 12/1997 |
| WO | WO 98/38961 | 9/1998 |
| WO | WO 98/39634 | 9/1998 |
| WO | WO 00/70350 | 11/2000 |

OTHER PUBLICATIONS

Ozdemir et al., "Hybrid Calibration Models: An Alternative to Calibration Transfer," Applied Spectroscopy, vol. 52, No. 4, pp. 599-603 (1998).

XP002146316—*Sigma Biochemikalien und reagenzien fur die Naturwissenschaftliche Forschung*, see "Probe-clip press-seal incubation chambers," Sigma Chemical Co., Germany, p. 2338 (1997).

Blank et al., "Transfer of Near-Infrared Multivarlate Calibrations without Standards, " Analytical Chemistry, vol. 68, No. 17, pp. 2987-2995 (1996).

Gemperline et al., "Appearance of Discontinuities in Spectra Transformed by the Piecewise Direct Instrument Standardization Procedure," Analytical Chemistry, vol. 68, No. 17, pp. 2913-2915 (1996).

Blanco et al., "Wavelenght Calibration Transfer Between Diode Array UV-Visible Spectrophotometers," Applied Spectroscopy, vol. 49, No. 5, pp. 593-597 (1995).

Funk et al., *Quality Assurance Chemistry*, VCH, New York, pp. 50 and 68-72 (1995).

Bouvaresse et al., "Calibration Transfer Across Near-Infrared Spectrometric Instruments Using Shenk's Algorithm: Effects of Different Standardisation Samples," Analytica Chimica Acta, vol. 297, pp. 405-416 (1994).

*Tietz Textbook of Clinical Chemistry* (2nd Ed.), "Measurement of Hemoglobin Concentration in Whole Blood," pp. 2020-2025 and 2069 (1994).

Wang et al., "Multivariate Instrument Standardization, " Analytical Chemistry, vol. 63, No. 23, pp. 2750-2756 (1991).

Heckman et al., "Transfer of Near-Infrared Monochromator Calibrations for Tobacco Constituents to Tilting-Filter Instruments,"Chimica Acta, vol. 192, 197-208 (1987).

Martinek, "Liquid Absorbance Standards for Ultraviolet, Visible, and Near Infrared Spectrophotometry," J. Amer. Med. Technol., vol. 40, pp. 20-216 (1978).

Harboe, "A Method for Determination of Hemoglobin In Plasma by Near-Ultraviolet Spectrophotometry," Scand. J. Clin. & Lab. Investigation, vol. 11, pp. 66-70 (1959).

Communication from European Patent Office in counterpart foreign application No. EP 04 253 225.9.

* cited by examiner

SPECTROSCOPIC METHOD AND APPARATUS FOR TOTAL HEMOGLOBIN MEASUREMENT

This application is a continuation-in-part of U.S. patent application Ser. No. 10/823,778, filed on Apr. 14, 2004, which is a continuation-in-part of U.S. patent application Ser. No. 10/805,290, filed on Mar. 22, 2004, now abandoned, which is a continuation of U.S. patent application Ser. No. 09/875,143, filed on Jun. 7, 2001, now U.S. Pat. No. 6,711,516, which is a continuation-in-part of U.S. patent application Ser. No. 09/773,495, filed on Feb. 2, 2001, now abandoned, which is a continuation-in-part of U.S. patent application Ser. No. 09/697,679U, filed on Oct. 27, 2000, now abandoned, which is a continuation-in-part of U.S. patent application Ser. No. 09/447,215, filed on Nov. 23, 1999, now U.S. Pat. No. 6,470,279.

This application is also a continuation-in-part of U.S. patent application Ser. No. 10/319,492, filed on Mar. 7, 2003, now U.S. Pat. No. 7,157,282, which is a continuation-in-part of U.S. patent application Ser. No. 10/023,869, filed Dec. 21, 2001, now U.S. Pat. No. 6,828,152.

This application is also a continuation-in-part of U.S. patent application Ser. No. 10/136,329, filed on May 2, 2002, now U.S. Pat. No. 6,949,384, which is a continuation-in-part of U.S. patent application Ser. No. 10/023,869, filed on Dec. 21, 2001, now U.S. Pat. No. 6,828,152.

This application is also a continuation-in-part of U.S. patent application Ser. No. 10/042,258, filed on Jan. 11, 2002, now U.S. Pat. No. 6,841,132, which is a continuation-in-part of U.S. patent application Ser. No. 09/958,933, filed on Jan. 23, 2002, now U.S. Pat. No. 6,582,964, which is the National Stage of International Application No. PCT/CA00/00549, filed May 11, 2000.

FIELD OF INVENTION

This invention relates to the field of spectroscopic measurement of Total Hemoglobin (Hb) in biological samples. The present invention provides methods and an apparatus for measuring Total-Hb in biological samples.

BACKGROUND OF THE INVENTION

Clinical laboratory tests are routinely performed on the serum or plasma of whole blood. In a routine assay, red blood cells (RBC) are separated from plasma by centrifugation, or RBC's and various plasma proteins are separated from serum by clotting prior to centrifugation. Hb, light-scattering substances like lipid particles, and bile pigments bilirubin (BR) and biliverdin (BV) are typical blood components, which will interfere with and affect spectroscopic and other blood analytical measurements of blood analytes. Such components are referred to as interferents, and they can be measured by spectroscopic methods. The presence of such interferents affects the ability to perform tests on the serum or plasma and as such can be said to compromise sample integrity.

CO-oximetry is a technique used to measure the major Hb species in whole blood, for example, Oxy-Hb, Deoxy-Hb, Met-Hb, Carboxy-Hb, and Sulf-Hb. The technique of CO-oximetry requires that the whole blood is collected in such a manner as to protect the sample from exposure to air, so as to minimize conversion of Deoxy-Hb into Oxy-Hb. Further, the technique requires that the RBC's be hemolyzed to provide an optically transparent sample in the cuvette for measurement. The most commonly used method of hemolyzing a whole blood sample is to expose the sample to the sound waves of an ultrasonic sound generator; chemical hemolyzing agents may also be used. Current methods of CO-oximetry use the extinction coefficient of the Hb species at different wavelengths, in the calibration algorithms. They are not designed to deal with the light-scattering effect created by RBC's, hence the requirement of a hemolyzing system. Some CO-oximetry methods, for example U.S. Pat. No. 4,997,769, suggest that they can mathematically deal with scattering of light by small particles, for example chylomicrons (an RBC is 1-2 orders of magnitude larger than a chylomicron), but a hemolyzing system is still required.

Current methods of measuring Total-Hemoglobin (Tot-Hb) in a sample, preferably use reagents, whereby the different Hb species like Oxy-hemoglobin (Oxy-Hb), Deoxy-Hemoglobin (Deoxy-Hb), Carboxy-Hemoglobin (Carboxy-Hb), and Met-Hemoglobin (Met-Hb) are converted to a single specie, which is then measured at one wavelength using spectroscopic methods; sometimes a second wavelength is also used. The reagents are usually noxious (e.g. potassium cyanide and azide), and there is a need for a reagentless method for measuring Hb in body fluids. Harboe (Harboe, M., 1959, A method of determination of hemoglobin in plasma by near ultraviolet spectrophotometry. Scand. J. Clin. Lab. Invest, pp. 66-70) and Tietz (Tietz Textbook of Clinical Chemistry, $3^{rd}$ Ed, 1999, pp 1674-1676; which is incorporated herein by reference), provide examples of reagentless spectroscopic methods for measuring Hb. Although Hb provides very large absorbance signals, the absorbance spectra of the Hb species exhibit significant differences. Reagentless spectroscopic methods are limited to samples that contain mostly Oxy-Hb and Deoxy-Hb. The Deoxy-Hb is usually converted into Oxy-Hb when the sample is exposed briefly to atmospheric oxygen. The largest source of errors in both methods (Harboe & Tietz) is the presence of Met-Hb. In U.S. Pat. No. 6,689,612 (Samsoondar), there is described the use of Total-Hb, Oxy-Hemoglobin (Oxy-Hb), and "Total-Hb minus Met-Hemoglobin (Met-Hb)," as indicators of hemolysis. Because the absorbance spectrum for Met-Hb is so different from the other Hb species, a calibration algorithm developed for Hb may be better at predicting "Total-Hb minus Met-Hb."

Met-Hb is an oxidation product of Hb and the Met-Hb form of the Hemoglobin-based (Hb-based) blood substitutes is also an oxidation product of Hemoglobin-based blood substitutes. Met-Hb from natural Hb, or Hb-based blood substitutes, cannot carry oxygen, and therefore Met-Hb, or Met-Hb form of the Hemoglobin-based blood substitutes are not functional Hb.

SUMMARY OF THE INVENTION

This invention relates to the field of spectroscopic measurement of Total Hemoglobin (Hb) in biological samples. The present invention provides methods and an apparatus for measuring Total-Hb in biological samples.

It is an object of the invention to provide an improved method and apparatus for measuring Total-Hb.

The present invention provides a method (A) of measuring Tot-Hb in a sample, comprising:

i) collecting an absorbance measurement of the sample using one or more than one first or second spectroscopic apparatus comprising a first primary calibration algorithm for one of Oxy-Hb, "Oxy-Hb plus Deoxy-Hb", or "Total-Hb minus Met-Hb", and one or more than one second primary calibration algorithm for one or more than one of Met-Hb, Carboxy-Hb, or Sulf-Hb, or comprising a third primary calibration algorithm obtained by adding terms of the first primary calibration algorithm and the second primary calibration algorithm together; and ii) predicting either:

a) a first value for one of Oxy-Hb, "Oxy-Hb plus Deoxy-Hb," or "Total-Hb minus Met-Hb", in the sample by applying the first primary calibration algorithm to an order derivative of absorbance of the sample at one or more than one wavelength of a standard set of wavelengths, and predicting one or more than one second value for one or more than one of Met-Hb, Carboxy-Hb, or Sulf-Hb in the sample by applying the second primary calibration algorithm to an order derivative of absorbance at one or more than one wavelength of a standard set of wavelengths, and adding the first value and the one or more than one second value together to provide a measurement of Total-Hb; or b) Total-Hb using the third primary calibration algorithm applied to an order derivative of absorbance of the sample at one or more than one wavelength of a standard set of wavelengths.

Furthermore, the sample may be one of whole blood, serum, plasma, urine, synovial fluid, lymphatic fluid, sputum, feces, or cerebrospinal fluid, and the Total-Hb, may be used as an indicator of hemolysis. Additionally, this invention pertains to the method described above wherein the sample may be exposed to atmospheric oxygen prior to the absorbance measurement.

The present invention also pertains to the method (A) described above, wherein in the step of collecting (step i)), the first primary calibration algorithm and the one or more than one second primary calibration algorithm are generated using an order derivative of absorbance at one or more than one wavelength of a standard set of wavelengths, obtained from one or more than one first apparatus using one or more than one calibration set having known reference values for one or more than one of Oxy-Hb, "Oxy-Hb plus Deoxy-Hb", "Total-Hb minus Met-Hb", Met-Hb, Carboxy-Hb, or Sulf-Hb, the first primary calibration algorithm is generated for one of Oxy-Hb, "Oxy-Hb plus Deoxy-Hb," or "Total-Hb minus Met-Hb", using an order derivative of absorbance at the one or more than one wavelength of a standard set of wavelengths, the known reference values, and a statistical technique and the one or more than one second primary calibration algorithm is generated for one or more than one of Met-Hb, Carboxy-Hb, or Sulf-Hb, using an order derivative of absorbance at the one or more than one wavelength of a standard set of wavelengths, the known reference values, and the statistical technique. Furthermore, the standard set of wavelengths may be selected from the range from about 300 nm to about 2500 nm, and the statistical technique may be selected from the group consisting of simple linear regression, multiple linear regression, and multivariate analysis. If the statistical technique is multivariate analysis, then it may be selected from the group consisting of partial least squares, principal component analysis, neural network, and genetic algorithm.

The present invention includes the method (A) described above, wherein the first primary calibration algorithm and the one or more than one second primary calibration algorithm, or the third primary calibration algorithm, are installed on, and in operative association with, a second apparatus, and in the step of collecting (step i), the absorbance of the sample is measured on the second apparatus to produce an absorbance measurement. Furthermore, the first primary calibration algorithm and the one ore more than one second primary calibration algorithm may be upgraded, using a small set of unique calibrator materials that are distinct from the primary calibration set The present invention also provides the method (A) described above, wherein the one or more than one apparatus is a second apparatus, and wherein a step of data pre-processing follows the step of collecting (step i) and precedes the step of predicting (Step ii). Furthermore, the step of data pre-processing include a process selected from the group consisting of: calculation of interpolated absorbances; smoothing of absorbances; calculation of a first and higher order derivative of absorbance; multiplicative scatter correction; data transformation; photometric correction, and a combination thereof.

The present invention provides a reagentless spectroscopic method (B) for measuring Total-Hb in a sample comprising:

i) collecting an absorbance measurement of the sample using one or more than one spectroscopic apparatus comprising a primary calibration algorithm for Total-Hb, the sample having been exposed to atmospheric oxygen; and ii) predicting a value for Total-Hb in the sample by applying the primary calibration algorithm to an order derivative of absorbance of the sample at one or more than one wavelength of a standard set of wavelengths, to provide a measurement of Total-Hb.

Furthermore, step of data pre-processing may follow the step of collecting (step i)), and before the step of predicting (step (v)). The step of data pre-processing may include a process selected from the group consisting of: calculation of interpolated absorbances; smoothing of absorbances; calculation of a first and higher order derivative of absorbance; multiplicative scatter correction; data transformation; photometric correction, and a combination thereof. The sample may be one of whole blood, serum, plasma, urine, synovial fluid, lymphatic fluid, sputum, feces, or cerebrospinal fluid, and the Total-Hb, may be used as an indicator of hemolysis. Additionally, this invention pertains to the method described above wherein the sample may be exposed to atmospheric oxygen prior to the absorbance measurement.

The present invention also pertains to the reagentless spectroscopic method described above (B), wherein in the step of collecting (step i)), the primary calibration algorithm for Total-Hb is generated using an order derivative of absorbance at one or more than one wavelength of a standard set of wavelengths obtained from one or more than one first apparatus, known reference values obtained from a primary calibration set, and a statistical technique, wherein each sample of the calibration set is exposed to atmospheric oxygen before spectroscopic measurement, and wherein the calibration set comprises known reference values from about 0 to about 100% of one or more than one of Oxy-Hb, Deoxy-Hb, Met-Hb, Carboxy-Hb, and Sulf-Hb. Furthermore, the primary calibration algorithm may be installed on, and be in operative association with, a second apparatus, and in the step of collecting (step i)), the absorbance of the sample is measured on the second apparatus to produce an absorbance measurement. Additionally, the first primary calibration algorithm may be upgraded using a small set of unique calibrator materials that are distinct from the primary calibration set prior to obtaining the absorbance measurement, and the standard set of wavelengths may be selected from the range from about 300 nm to about 2500 nm, or any amount therebetween. The statistical technique may be selected from the group consisting of simple linear regression, multiple linear regression, and multivariate analysis. If the statistical technique is multivariate analysis, then it may be selected from the group consisting of partial least squares, principal component analysis, neural network, and genetic algorithm.

The present invention also provides the reagentless spectroscopic method (B), wherein measuring the proportion of Total-Hb that is in the form of Met-Hb provides a method of monitoring degradation or reversal of degradation of one or more than one Hb-based blood substitute in the sample.

The present invention provides a spectroscopic apparatus, comprising:

a) a source of electromagnetic radiation (EMR);

b) a first aperture located between the source of EMR and a sample slot to produce a light path therebetween;

c) the sample slot in the apparatus for receiving a sample vessel to be placed within the light path;

d) a second aperture located in the light path, between the sample slot and one or more than one photodetector, the one or more than one photodetector in operative association with the spectroscopic apparatus; and either e) a first primary calibration algorithm in operative association with the spectroscopic apparatus, the first primary calibration algorithm generated for one of Oxy-Hb, "Oxy-Hb plus Deoxy-Hb," or "Total-Hb minus Met-Hb", using an order derivative of absorbance at the one or more than one wavelength of a standard set of wavelengths obtained from one or more than one first apparatus using one or more than one calibration set having known reference values for one or more than one of Oxy-Hb, "Oxy-Hb plus Deoxy-Hb", "Total-Hb minus Met-Hb", Met-Hb, Carboxy-Hb, or Sulf-Hb, and a statistical technique, and one or more than one second primary calibration algorithm in operative association with the spectroscopic apparatus, the one or more than one second primary calibration algorithm generated for one or more than one of Met-Hb, Carboxy-Hb, or Sulf-Hb, using an order derivative of absorbance at the one or more than one wavelength of a standard set of wavelengths, the known reference values, and the statistical technique; or f) a third primary calibration algorithm in operative association with the spectroscopic apparatus, the third primary calibration algorithm obtained by adding the terms of the first primary calibration algorithm and the terms of the one or more than one second primary calibration algorithm together.

The present invention also provides a spectroscopic apparatus, comprising:

a) a source of electromagnetic radiation (EMR);

b) a first aperture located between the source of EMR and a sample slot to produce a light path therebetween;

c) the sample slot in the apparatus for receiving a sample vessel to be placed within the light path;

d) a second aperture located in the light path, between the sample slot and one or more than one photodetector, the one or more than one photodetector in operative association with the spectroscopic apparatus; and e) one or more than one first primary calibration algorithm in operative association with the spectroscopic apparatus, the primary calibration algorithm for Total-Hb is generated using an order derivative of absorbance at one or more than one wavelength of a standard set of wavelengths obtained from one or more than one first apparatus, known reference values obtained from a primary calibration set, and a statistical technique, wherein each sample of the calibration set is exposed to atmospheric oxygen before spectroscopic measurement, and wherein the calibration set comprises known reference values from about 0 to about 100% of one or more than one of Oxy-Hb, Deoxy-Hb, Met-Hb, Carboxy-Hb, and Sulf-Hb.

The present invention also provides for a method (C) of monitoring degradation or reversal of degradation of one or more Hb-based blood substitutes in a sample comprising:

i) determining a first concentration of Met-Hb, and a first concentration of the one or more than one Hb-based blood substitutes in the sample, by applying a first primary calibration algorithm for the Met-Hb, and a second primary calibration algorithm for the one or more than one Hb-based blood substitutes, to an order derivative of absorbance of the sample at one or more wavelength of a standard set of wavelengths;

ii) determining a second concentration of the Met-Hb and a second concentration of the one or more than one Hb-based blood substitutes in the sample at a second time, by applying a first primary calibration algorithm for the Met-Hb, and the second primary calibration algorithm for the one or more than one Hb-based blood substitutes to an order derivative of absorbance of the sample at one or more wavelength of a standard set of wavelengths; and iii) calculating a first proportion of the one or more than one Hb-based blood substitutes that is in the form of Met-Hb using the first concentration of Met-Hb and the first concentration of the one or more than one Hb-based blood substitutes, and calculating a second proportion of the one or more than one Hb-based blood substitutes that is in the form of Met-Hb using the second concentration of Met-Hb and the second concentration of the one or more than one Hb-based blood substitutes;

where an increase in the second proportion, when compared to the first proportion is an indication of degradation of the one or more than one blood substitute, and a decrease in the second proportion, when compared to the first proportion is an indication of a reversal of degradation of the one or more than one Hb-based blood substitute, thereby monitoring degradation or reversal of degradation of the one or more Hb-based blood substitutes.

Also provided in the present invention is a method (D) of determining degradation of one or more than one Hb-based blood substitute in a sample, comprising:

i) measuring an absorbance of the sample at one or more than one wavelengths of a standard set of wavelengths using a spectroscopic apparatus comprising, a calibration algorithm for Met-Hb and one or more than one calibration algorithm for the one or more than one Hb-based blood substitute;

ii) calculating a first concentration of the Met-Hb from the absorbance, by applying the calibration algorithm for Met-Hb to an order derivative of the absorbance, and calculating a second concentration of the one or more Hb-based blood substitute from the absorbance, by applying the one or more than one calibration algorithm for the Hb-based blood substitutes to an order derivative of the absorbance;

where, if the first concentration of the Met-Hb is greater than or equal to 3% of the second concentration of the one or more than one Hb-Based blood substitute, then this indicates degradation of the one or more than one Hb-based blood substitute.

Preferably, the sample is selected from the group consisting of, a whole blood sample obtained from a patient infused with one or more than one Hb-based blood substitutes, a serum sample obtained from a patient infused with one or more Hb-based blood substitutes, a plasma sample obtained from a patient infused with one or more Hb-based blood substitutes, and a stock Hb-based blood substitute.

The present invention pertains to either the method (C) or (D) described above wherein in the step of measuring or determining (step i), the spectroscopic apparatus comprises:

a) one or more than one source of electromagnetic radiation (EMR) that produce a light path;

b) one or more than one photodetector in alignment with the light path;

c) a sample slot for receiving a sample vessel to be placed within the light path;

d) one or more than one primary calibration algorithm in operative association with the spectroscopic apparatus, the one or more than one primary calibration algorithm developed using one or more than one other apparatus, or one or more than one upgraded primary calibration algorithm in operative association with the spectroscopic apparatus.

Additionally, the sample vessel may be selected from the group consisting of, a cuvette, a sample tab, a pipette tip, tubing, a labeled test tube, an unlabeled test tube, blood bag tubing, a transparent sample container, a translucent sample container, and a flow-through cuvette.

The present invention describes a method for measuring an analyte, for example, Total-Hb more accurately, by a spectroscopic method, and also for measuring at the same time, Met-Hb from natural Hb or Hb-based blood substitutes. An apparatus for use in analysing the analyte is also described.

When the sample is whole blood, the present invention does not require a hemolyzing system or agent, and the sample may be exposed to air. Exposure to air may be desired if a measurement of Deoxy-Hb is not required, as Deoxy-Hb will readily change to Oxy-Hb when exposed to atmospheric oxygen. By way of illustration, the equivalent partial pressure of oxygen in a whole blood sample that is exposed to atmospheric oxygen is about 150 mm mercury (Hg), i.e., 20% of 760 mm Hg (atmospheric pressure), and is much greater than the partial pressure of oxygen in arterial blood, which is 80-100 mm Hg in a healthy adult; greater than 95% Hb in arterial blood is in the form of Oxy-Hb, assuming there is no abnormal levels of Met-Hb, Carboxy-Hb and Sulf-Hb.

Furthermore the present invention provides a first or second order derivative of absorbance may be used with the methods provided above, for example but not limited to Method (A), (B), (C) or (D) to overcome the scattering of light by particles like chylomicrons and RBC's. However, it should be understood that any order derivative of absorbance, including zero order, is within the scope of the invention.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 4 shows various aspects of a sample tab that may be used in accordance with the present invention. A reflector may be positioned underneath the sample tab for use in reflection mode.

FIG. 5 shows various aspects of a sample tab used in accordance with the present invention. The sample tab is shown for use in transmission mode.

FIG. 6 shows more details of an apparatus of the present invention illustrated in FIG. 5.

FIG. 7 shows various aspects of an alternate embodiment of a sample tab used in the present invention.

DETAILED DESCRIPTION

Figure 1:
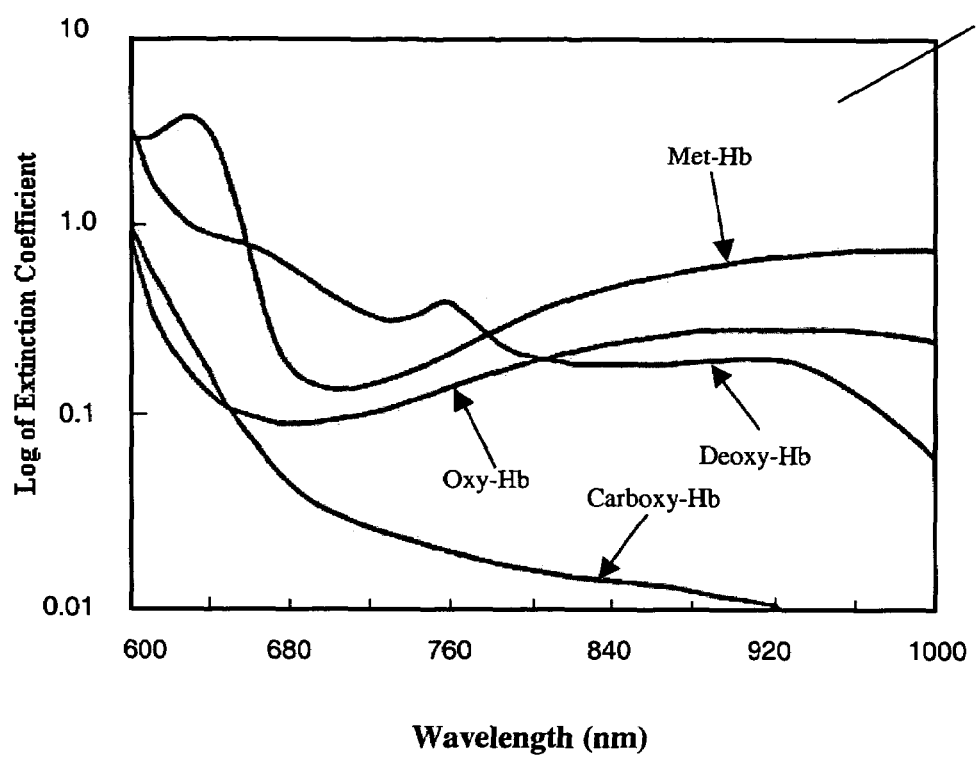
FIG. 1 shows a graphic representation of the absorbance spectra of four different hemoglobin species, as shown, in the wavelength range of 600-1000 nm plotted on the x-axis, and log of extinction coefficient plotted on the y-axis.

This invention relates to the field of spectroscopic measurement of Total Hemoglobin (Hb) in biological samples. The present invention provides methods and an apparatus for measuring Total-Hb in biological samples.

The following description is of a preferred embodiment.

The present invention provides a method of measuring Tot-Hb in a sample. This method may comprise:

i) collecting an absorbance measurement of the sample using one or more than one first or second spectroscopic apparatus comprising a first primary calibration algorithm for one of Oxy-Hb, "Oxy-Hb plus Deoxy-Hb", or "Total-Hb minus Met-Hb", and one or more than one second primary calibration algorithm for one or more than one of Met-Hb, Carboxy-Hb, or Sulf-Hb, or comprising a third primary calibration algorithm obtained by adding terms of the first primary calibration algorithm and the terms of the one or more than one second primary calibration algorithm together; and ii) predicting either:

a) a first value for one of Oxy-Hb, "Oxy-Hb plus Deoxy-Hb," or "Total-Hb minus Met-Hb", in the sample by applying the first primary calibration algorithm to an order derivative of absorbance of the sample at one or more than one wavelength of a standard set of wavelengths, and predicting one or more than one second value for one or more than one of Met-Hb, Carboxy-Hb, or Sulf-Hb in the sample by applying the second primary calibration algorithm to an order derivative of absorbance at one or more than one wavelength of a standard set of wavelengths, and adding the first value and the one or more than one second value together to provide a measurement of Total-Hb; or b) Total-Hb using the third primary calibration algorithm applied to an order derivative of absorbance of the sample at one or more than one wavelength of a standard set of wavelengths.

Additionally, the sample may be exposed to atmospheric oxygen prior to the absorbance measurement. Furthermore:

in the step of collecting (step i), above), the first primary calibration algorithm and the one or more than one second primary calibration algorithm may be generated using an order derivative of absorbance at one or more than one wavelength of a standard set of wavelengths, obtained from one or more than one first apparatus using one or more than one calibration set having known reference values for one or more than one of Oxy-Hb, "Oxy-Hb plus Deoxy-Hb", "Total-Hb minus Met-Hb", Met-Hb, Carboxy-Hb, or Sulf-Hb, the first primary calibration algorithm may be generated for one of Oxy-Hb, "Oxy-Hb plus Deoxy-Hb," or "Total-Hb minus Met-Hb", using an order derivative of absorbance at the one or more than one wavelength of a standard set of wavelengths, the known reference values, and a statistical technique, and the one or more than one second primary calibration algorithm may be generated for one or more than one of Met-Hb, Carboxy-Hb, or Sulf-Hb, using an order derivative of absorbance at the one or more than one wavelength of a standard set of wavelengths, the known reference values, and the statistical technique.

The present invention also provides a reagentless spectroscopic method for measuring Total-Hb in a sample. This method may comprise:

i) collecting an absorbance measurement of the sample using one or more than one spectroscopic apparatus comprising a primary calibration algorithm for Total-Hb, the sample having been exposed to atmospheric oxygen; and ii) predicting a value for Total-Hb in the sample by applying the primary calibration algorithm to an order derivative of absorbance of the sample at one or more than one wavelength of a standard set of wavelengths, to provide a measurement of Total-Hb.

The present invention provides a spectroscopic apparatus. This apparatus may be used for determining the concentration or presence of a desired analyte within a sample, and may comprise:

a) a source of electromagnetic radiation (EMR) capable of producing wavelengths, for example, from about 300 nm to about 2500 nm, or any wavelength therebetween;

b) a first aperture located between the source of EMR and a sample slot to produce a light path therebetween;

c) the sample slot in the apparatus for receiving a sample vessel to be placed within the light path;

d) a second aperture located in the light path, between the sample slot and one or more than one photodetector, the one or more than one photodetector in operative association with the spectroscopic apparatus; and e) one or more than one primary calibration algorithm in operative association with the spectroscopic apparatus, the one or more than one primary calibration algorithm developed using one or more than one other apparatus, or one or more than one upgraded primary calibration algorithm in operative association with the spectroscopic apparatus.

Also disclosed herein is a method of monitoring degradation or reversal of degradation of one or more than one Hb-based blood substitute in a sample. This method may comprise:

i) measuring the sample using a spectroscopic apparatus comprising a calibration algorithm for Met-Hb, at one or more than one wavelengths of a standard set of wavelengths, to obtain an absorbance;

ii) determining a first concentration of the Met-Hb from the absorbance, by applying the calibration algorithm, to an order derivative of the absorbance;

iii) determining a second concentration of the Met-Hb in the sample at a second time;

where degradation of the one or more than one blood substitute is indicated by an increase in the second concentration compared to the first concentration, and where reversal of degradation of the one or more than one blood substitute is indicated by a decrease in the second concentration when compared to the first concentration.

The present invention also provides for an alternate method of monitoring degradation of one or more Hb-based blood substitutes in a sample comprising:

i) determining a first concentration of Met-Hb, and a second concentration of the one or more than one Hb-based blood substitutes in the sample, by applying a first calibration algorithm for the Met-Hb, and a second calibration algorithm for the one or more than one Hb-based blood substitutes, to an order derivative of absorbance of the sample at one or more than one wavelengths of a standard set of wavelengths;

ii) calculating a proportion of the one or more than one Hb-based substitutes that is in the form of Met-Hb; and iii) using the proportion of Met-Hb as a measurement of degradation of the one or more than one Hb-based blood substitutes to monitoring degradation of the one or more than one Hb-based blood substitutes. For example, if the first concentration of the Met-Hb is greater than or equal to 3% of the second concentration of the one or more than one Hb-Based blood substitute, than this indicates degradation of the one or more than one Hb-based blood substitute.

Technical terms used herein are defined below for clarification.

By "analyte" it is meant a substance being measured in a sample. Examples of samples within which analytes are to be measured include, but are not limited to, biological samples for example whole blood, serum, plasma, urine, synovial fluid and cerebrospinal fluid, sputum, lymphatic fluid, semen and feces, or non-biological samples selected from the group consisting of milk, cheese, cottage cheese, yogourt, ice cream, wine, and other beverages, semi-solid food and soft solid food.

By "absorbance" it is meant a reduction of light intensity caused by a sample. According to Beer's law, Absorbance=Log(1/Transmitted light), which applies to non-light-scattering samples. The measured parameter is the amount of light transmitted through a sample, and the transmitted light (or transmittance or transmission) is then converted to absorbance units. When a sample is light-scattering and Beer's law is applied, an apparatus cannot distinguish "true absorbance" from loss of light due to scattering, hence the term "apparent absorbance" should be used. It should be understood that when the term "absorbance" is used, it could mean either "true absorbance" or "apparent absorbance," or both, since it is not always obvious whether the sample is light-scattering or non-light-scattering. Although examples are given with respect to absorbance, it should be understood that absorbance can be replaced with Log(1/Reflectance), when reflectance (or reflection) is measured instead of transmittance, and reflectance measurement is within the scope of the present invention. It should be understood that the terms transmittance and transmission are sometimes used interchangeably. It should also be understood that the terms reflectance and reflection are sometimes used interchangeably.

By "actual absorbance" or "measured absorbance" it is meant the absorbance value, or absorbance measurement, or simply absorbance of a sample or calibrator material that is provided by the apparatus at one or more given wavelength(s) from a wavelength calibration table of the apparatus.

By "adjusted interpolated absorbance" it is meant the value of the interpolated absorbance after photometric correction is applied specifically to the interpolated absorbance.

By "blood bag tubing" it is meant the tubing connecting a first bag made of any suitable polymer or plastic that contains whole blood and a second bag made of any suitable polymer or plastic that may contain plasma obtained from the first bag. The tubing and bags may be made from transparent or translucent flexible polymer or plastic.

By "blood substitute" it is meant any substance that can be used instead of whole blood or red blood cells (RBC's) for blood transfusion. Some advantages of using a blood substitute instead of blood or red blood cells are as follows: blood substitutes are expected to be universally compatible with all blood types, therefore cross-matching will not be necessary; maximum storage time of blood is 42 days, whereas the blood substitutes could have a much longer shelf-life; the purification process of the blood substitute may include heat treatment, which could eliminate the threat of hazardous viruses.

Another type of blood substitute has been reported, which is characterized as a milky-white emulsion containing tiny beads of perfluorocarbons within a suitable surfactant. These "milky-white" blood substitutes may be referred to as "perfluorocarbon-like" blood substitutes. It should be understood that the term perfluorocarbon-like blood substitutes refers to all blood substitutes that are characterized as milky-white emulsions. Due to the beads contained with these blood substitutes, "perfluorocarbon-like" blood substitutes are characterized as comprising a component that scatters light.

By "interferents" it is meant an analyte whose presence in a sample, for example a serum or plasma sample, interferes with the determination of the presence, the quantification, or both, of another analyte within the sample.

By "calibration algorithm transfer" it is meant the process of transferring a calibration algorithm from a first apparatus to a second apparatus, whereby the calibration algorithm is brought into operative association with the second apparatus, so that the algorithm may be applied by the second apparatus for predicting the concentration of a measured analyte of interest in a sample. For the convenience of transferring a calibration algorithm form a first apparatus to a second apparatus, it is preferred that a standard set of wavelengths are used. The process of calibration algorithm transfer is disclosed in U.S. Pat. No. 6,651,015 (Samsoondar; which is incorporated herein by reference). The method used to calibrate a first apparatus, wherein the apparatus can be used to measure the concentration of at least one analyte, is referred to as primary calibration. Primary calibration is a complex process and is described herein under the title "Primary Calibration." Due to its complexity, performance of primary calibration on every apparatus is not practical or desirable.

The present invention provides a simple alternative that allows an apparatus, for example a second apparatus, to function as though it was calibrated by the process of primary calibration. The second apparatus need not be calibrated in the same way in which the first apparatus was calibrated, in that there is no need to conduct a primary calibration using the second apparatus. It is preferred that the first and second apparatus are similar, however, this is not always required, depending upon the accuracy or type of measurement required by using the second apparatus.

The present inventor has found that for a given analyte, a "primary calibration algorithm" developed using one or more "first apparatus" can be transferred onto a "second apparatus," and the second apparatus used directly following calibration algorithm transfer. Additionally, the transferred primary calibration on the second apparatus may be upgraded, if desired, using a small set of unique calibrator materials that are distinct from the primary calibration set. Preferably, the small set of unique calibrator materials are similar to the samples of the primary calibration set.

By "data pre-processing" it is meant any mathematical manipulation of spectroscopic data, which can be used to facilitate measurement of an analyte on an apparatus, including a first, second, or both, apparatus. Examples of data pre-processing, which should not be considered limiting in any way are:
calculation of absorbance of electromagnetic radiation (EMR) transmitted through or reflected from a sample;
calculation of interpolated absorbances;
smoothing of absorbances; calculation of a first and higher order derivative of absorbance;
multiplicative scatter correction;
data transformation; and
photometric correction.

It should be understood that any one or more forms of data pre-processing can be used prior to development of a calibration algorithm, and any one or more forms of data pre-processing can be used on the data from a second apparatus, prior to applying the calibration algorithm for calculating the concentration of an analyte. A non-limiting example of smoothing includes averaging of data.

By "Data Transformation" it is meant any mathematical technique that can be applied to either spectroscopic data or analyte concentration data. Examples of data transformation, which should not be considered limiting in any way, include Fourier Transformation of spectroscopic data, and calculation of the log or anti-log of an analyte concentration. It should be understood that smoothing can also be considered as data transformation, for example when the Savitzky-Golay method (Savitzky and Golay 1964, Anal. Chem., 36:1627-1638) is used.

By "derivative of absorbance" it is meant an order derivative of the absorbance. A zero order derivative of absorbance is the measured absorbance. The first order derivative of absorbance at a particular wavelength is the slope of the absorbance spectrum at that wavelength; the second order derivative of absorbance at a particular wavelength is the slope of the first derivative absorbance spectrum at the wavelength. Higher order derivative (third, fourth etc.) of absorbance can similarly be obtained by taking the slope of the derivative absorbance spectrum of the order immediately below (second, third etc.) Methods of calculating a derivative of absorbance at a particular wavelength are well known by those skilled in the art.

Calculation of the first derivative of absorbance at a particular wavelength may consist in taking the difference in absorbances at the two wavelengths that encompass the wavelength of interest. Other methods of calculating derivative of absorbance may use the absorbances at several different wavelengths, where smoothing is an integral part of the derivative process. It should be understood that with a greater degree of smoothing, there is also a greater loss of signal details in the absorbance spectrum or the order derivative of the absorbance spectrum. The minimum number of wavelengths that may be used to calculate a derivative of absorbance is two wavelengths. Smoothing, data transformation, and calculation of order derivatives of absorbances are non-limiting examples of data pre-processing. Other forms of data pre-processing, as described above, may be performed either before or after calculation of an order derivative of absorbance, for example, but not limited to, multiplicative scatter correction.

By "first apparatus" it is meant an apparatus used to develop one or more than one primary calibration algorithm. One or more than one first apparatus may be used to develop a primary calibration algorithm.

By INTRALIPID™ (IL) it is meant a lipid emulsion that simulates naturally occurring chylomicrons in blood. IL is one example of such an emulsion. The major cause of turbidity in serum and plasma is fat particles, for example chylomicrons, therefore IL, or other lipid emulsions may be used to simulate turbidity in blood. The term "simulator of turbidity" is used to refer to the "analyte" measured to quantify turbidity.

By "indicator of hemolysis" it is meant any substance present within a red blood cell (RBC) and not present in the plasma that surrounds the RBC. An example of an indicator of hemolysis includes, but is not limited to, Total-Hb, Oxy-Hb or "Total-Hb minus Met-Hb." A sample of known Oxy-Hb concentration where the Oxy-Hb fraction is about 95% or the Total-Hb, can be considered to have a Total-Hb concentration of the same value as the Oxy-Hb concentration. Similarly, a sample of known Total-Hb concentration that comprises about 95% Oxy-Hb, can be considered to have an Oxy-Hb concentration of the same value as the Total-Hb concentration. Acceptability of the approximation of Total-Hb or Oxy-Hb concentration, depends on the required accuracy of the predicted value of the Total-Hb or the Oxy-Hb.

By "mapping" it is meant a process of associating an interpolated absorbance value with a standard wavelength.

"Multiplicative scatter correction" (also known as multiplicative signal correction) is a mathematical technique that may be used to remove at least some of the light scattering effect in the spectroscopic data obtained from a sample set. The technique rotates each absorbance spectrum so that it fits as closely as possible to the mean spectrum. The technique is described in more details in: Martens, H and Naes, T (Multivariate Calibration, 1993, Published by John Wiley & Sons); and Osborne, B. G., Fearn, T & Hindle, P. H. (Practical NIR Spectroscopy with Applications in Food and Beverage Analysis, 1993, Published by Longman Scientific & Technical), both of which are incorporated herein by reference. It should be understood that the mean spectrum for a sample set can be obtained after combining one or more than one sample absorbance measurement obtained from one or more than one apparatus.

By "photometric correction" or "absorbance adjustment" it is meant an adjustment made to an absorbance of a sample tested on one apparatus to make it appear as if the sample was tested on another apparatus. The amount of photometric correction is determined by the slope ("m") and y-intercept ("c") of the linear regression equation of the form "y=mx+c," obtained from the absorbances obtained from a set of calibrators on both the first apparatus, and a second apparatus during the process of calibration algorithm transfer. The resulting absorbance after photometric correction is referred to as adjusted absorbance or corrected absorbance.

By "pixeldispersion" it is meant, the wavelengths encompassed by two adjacent pixels of a linear diode array, usually measured in nanometers (nm) per pixel. For example, if two lasers of 600 nm and 900 nm are used for wavelength calibration, and they are projected on pixel 20 and pixel 220 respectively, that means 300 nm (i.e., 900-600 nm) are encompassed by 200 pixels (i.e., 220-20 pixels). Therefore the pixeldispersion is calculated to be 1.5 nm per pixel (i.e., 300 nm divided by 200 pixels). Alternatively, a predetermined pixeldispersion may be used, in which case, only a single laser of known wavelength or narrow bandpass filter that provides EMR of a known wavelength, is required to assign a wavelength to a pixel.

By "primary calibration" it is meant a process used to develop a primary calibration algorithm for a first apparatus for an analyte or optionally for more than one first apparatus. Typically, the sample set used for primary calibration is relatively large, and the samples are natural or very close to natural samples. The primary calibration set should include all the variability expected in a sample, in order to develop robust calibration algorithm(s). Furthermore, one, or more than one sample of the primary calibration set could be measured on one or more than one first apparatus and combined, in order to develop a more robust calibration algorithm(s) that also includes inter-apparatus variability. Such a calibration algorithm would be developed using a combination of measurements obtained from one, or more than one, similar apparatus.

Any form of statistical data analysis and optionally any form of data pre-processing, for example but not limited to, smoothing, calculation of first and higher order derivative of absorbance, photometric correction, data transformation, interpolation of absorbance, or multiplicative scatter correction, may be used, depending on the required accuracy of the analyte prediction. For example, by including data from more than one first apparatus, a lower level of precision and hence a lower level of accuracy (poor precision translates into poor accuracy) may be obtained across many second apparatus. Such a type of primary calibration would be suitable if a simple yes/no answer to the presence of an analyte in a sample is all that is required, and is within the scope of this invention.

If desired, a small set of unique samples which are not part of the primary calibration set can be measured on a second apparatus, and the data combined with some or all of the original data from the primary calibration set, to develop one, or more than one, "upgraded primary calibration algorithm." Preferably, the small set of unique samples are similar to the samples of the primary calibration set. Zero order derivative of absorbance (also referred to as raw absorbance) or any order derivative of absorbance may be used in the calibration process with second order derivative of absorbance being preferred, and first order derivative of absorbance being more preferred.

By "primary calibration algorithm" it is meant a mathematical equation, for example, but not limited to a linear combination of the type $Y=A(x)+B(x_1)+\ldots+C$ where Y (the dependant variable) is the concentration of a given analyte, A, B and C are constants and $x, x_1, \ldots$ are the order derivative of absorbance values (the independent variables) at specified wavelengths. The right side of the equation consists of the summation of "terms" of the equation. The terms of more than one equation can be added, for example, which should not be considered limiting in any way, the terms of two equations having the form:

$$Y_1 = A_1(x) + B_1(x_1) + C_1 \text{ and}$$

$$Y_2 = A_2(x) + B_2(x_1) + C_2,$$

can be added to produce a single equation of the form:

$$(Y_1+Y_2) = A_1(x) + B_1(x_1) + C_1 + A_2(x) + B_2(x_1) + C_2, \text{ or}$$

$$(Y_1+Y_2) = (A_1+A_2)(x) + (B_1+B_2)(x_1) + (C_1+C_2).$$

It should be understood that non-linear equations are within the scope of the present invention (e.g. Equations 16 and 17, Example 5). The equation is preferably obtained by multiple linear regression of a sample set, but other statistical techniques for example but not limited to, simple linear regression, PLS (partial least squares regression) and PCA (principle component analysis) may also be used and are within the scope of this invention. The sample set used for primary calibration is relatively large (see above), and the samples are natural or very close to natural samples. The primary calibration set should include all the variability expected in a sample, in order to develop robust calibration algorithm(s). The term "calibration algorithm" when used and unless otherwise specified, means the primary calibration algorithm, or any modification of the primary calibration algorithm (for example an upgraded primary calibration algorithm), whereby the modification is for improvement in accuracy of predicted values of an analyte, or to facilitate use of the primary calibration algorithm on another apparatus that was not calibrated as the first apparatus.

Primary calibration algorithms may be developed by trial-and-error, without using the absorbtivity or molar extinction coefficient (sometimes simply referred to as absorbtivity or extinction coefficient) per wavelength, for the analyte to be measured. When a primary calibration algorithm is installed on a spectroscopic apparatus used for determining the concentration of an analyte in a sample, the primary calibration algorithm is to be in operative association with the spectroscopic apparatus within which it is installed. As noted above, a primary calibration algorithm is typically developed using a first apparatus and transferred onto a second apparatus for use in the second apparatus. Furthermore, a primary calibration algorithm that is in operative association with the spectroscopic apparatus may be an upgraded primary calibration algorithm that was developed on a first apparatus, transferred to a second apparatus and upgraded after transfer, using for example, a small set of unique calibrators that were not part of the primary calibration set. However, it is to be understood that a primary calibration algorithm may be transferred from the first apparatus for use in a second apparatus and used directly, without any further modifications, or upgrading, of the primary calibration algorithm. A primary calibration algorithm that is in operative association with the spectroscopic apparatus may be installed on ROM, EPROM, EEPROM, microcontroller, microprocessor, internal or external memory device, for example but not limited to a disc, a CD, a memory stick, a flash memory card, or similar device, of the spectroscopic apparatus.

The term "calibration algorithm" when used and unless otherwise specified, means the primary calibration algorithm, or any modification of the primary calibration algorithm, whereby the modification is for improvement in accuracy of predicted values of an analyte, or to facilitate use of the primary calibration algorithm on another apparatus (e.g. a second apparatus) that was not calibrated as the first apparatus.

By "primary calibration set" it is meant the samples used for primary calibration.

By "primary calibration wavelength(s)" it is meant the wavelength(s) used in a primary calibration algorithm.

By "principal calibration wavelength" it is meant a wavelength of the primary calibration algorithm exhibiting a high correlation between an order derivative of absorbance, and the analyte concentration. The principal calibration wavelength may be different for the same analyte in different compositions. The primary calibration algorithm may optionally comprise one or more other wavelengths exhibiting low correlations between an order derivative of the absorbance and the analyte concentration. These other wavelengths are referred to as secondary calibration wavelengths. Secondary calibration wavelengths add robustness to the primary calibration algorithm especially in the presence of interferents that may have absorption bands overlapping that of the principal calibration wavelength(s) and therefore affect the correlation between the absorbance at the principal calibration wavelength and the analyte concentration.

A continuous spectral segment having a negative slope of from about 5 to about 400 nm or an amount there between, or from about 5 to about 200 nm or an amount there between, that contains at least one principal calibration wavelength is referred to as a "principal calibration section." For development of primary calibration algorithm, any statistical technique may be used for example, which should not be considered limiting in any way, simple linear regression, multiple linear regression, and multivariate data analysis. Examples of multivariate data analysis, which should not be considered limiting in any way, are Principal Component Analysis (PCA), Principal Component Regression (PCR), Partial Least Squares regression (PLS), and Neural networks. It should be understood that when multivariate analysis is used to develop a primary calibration algorithm, the primary calibration algorithm could contain many wavelengths at which high correlations between an order derivative of absorbance at respective wavelengths and the analyte concentration is observed.

By "predicted value," it is meant a value of an analyte obtained when the primary calibration algorithm for the analyte is applied to an order derivative of absorbance of a sample. As indicated earlier, a primary calibration algorithm is an equation comprising, for example, a predicted value of the analyte as the dependant variable, and a summation of a constant and one or more other terms. Each of the other terms is the product of a constant and an independent variable (see Examples 1 to 7). The independent variable is the order derivative of absorbance of the sample at a specific wavelength. It is to be understood that the predicted value need not necessarily be reported as a discrete concentration value, but may also include semi-quantitative or qualitative (e.g Yes/No) values.

By "reference value" of an analyte, it is meant the value of the analyte assigned to a sample. The reference value can be zero or any value above zero. A reference value is typically estimated by a method known within the art, which has a suitable level of accuracy. For example which is not to be considered limiting in any manner, known amounts of an analyte added to a sample can be used as the reference value, or, as in the case of an indicator of hemolysis, the indicator of hemolysis can be measured. In the case of an indicator of hemolysis, the preferred indicators are Total-Hb, Oxy-Hb and "Total-Hb minus Met-Hb".

The cyanmethemoglobin (cyanMet-Hb) method, which is well known to a person of skill in the art will measure all the Hb species present, i.e., Oxy-Hb, Deoxy-Hb, Carboxy-Hb and Met-Hb. Oxy-Hb can be measured by known reagentless spectroscopic methods, for example Harboe or Tietz (Harboe, M., 1959, A method of determination of hemoglobin in plasma by near ultraviolet spectrophotometry. Scand. J. Clin. Lab. Invest., pp. 66-70; Tietz Textbook of Clinical Chemistry, $3^{rd}$ Ed, 1999, pp 1674-1676; which is incorporated herein by reference). The Hb species actually measured by the reagentless spectroscopic apparatus depends on both the reference method used to measure the analyte, and the substances included in the samples of the primary calibration set.

By approximation, a sample of known Oxy-Hb concentration where the Oxy-Hb fraction is about 95% of the Total-Hb, can be considered to have a Total-Hb concentration of same value as the Oxy-Hb concentration. Similarly, a sample of known Total-Hb concentration that comprises about 95% Oxy-Hb, can be considered to have an Oxy-Hb concentration of the same value as the Total-Hb concentration. Also, by approximation, the concentrations of the Oxy-Hb, the "Oxy-Hb plus Deoxy-Hb," and the "Total-Hb minus Met-Hb," can be considered to be of the same value if the Oxy-Hb accounts for about 95% of the "Oxy-Hb plus Deoxy-Hb, or " 95% of "Total-Hb minus Met-Hb," in the sample, and similarly if the "Oxy-Hb plus Deoxy-Hb," or the "Total-Hb minus Met-Hb," in the sample, comprises about 95% Oxy-Hb.

By "sample" or "samples" it is meant a biological or non-biological fluids, a biological or non-biological semi-solid, or a biological or non-biological solid exhibiting one or more properties that may be measured spectroscopically. A sample typically comprises one or more than one analytes. Examples of a sample include, but are not limited to, a calibrator, whole blood, serum, plasma, urine, synovial fluid, lymphatic fluid, sputum, feces, cerebrospinal fluid, dairy products, beverages, a body part, for example but not limited to, a finger, arm, ear lobe, or a pharmaceutical tablet. Biological samples are not limited to humans, and may be obtained from any desired species, for example but not limited to any animal.

By "sample vessel" it is meant any transparent or translucent container capable of holding a sample to enable measurement of absorbance, reflectance, or both absorbance and reflectance of EMR from the sample. Examples of a sample vessel includes, but is not limited to, a sample tab, a pipette tip, tubing, a cuvette, a labeled test tube, an unlabeled test tube, blood bag tubing, a transparent sample container, and a translucent sample container. The sample vessel may be inserted within a sample slot of spectroscopic apparatus.

In the case of a cuvette, it should be understood that the cuvette could be designed as a flow-through cuvette, which requires that the sample be injected into the reuseable cuvette. However, a flow-through cuvette is not preferred due to the requirement of a wash system, but a flow-through cuvette is still considered to be within the scope of the present invention. The sample vessel may optionally contain one or more reagents. In the case of a body part, a receptor is required instead of a sample vessel.

The present invention need not be limited to a reagentless system, and the use of one or more reagents in the sample vessel is regarded as an enhancement of a reagentless system. Lilja et al in U.S. Pat. No. 4,088,448 describe a cuvette for sampling, with a cavity that is defined by two planar surfaces, which are placed at a predetermined distance from one another, wherein the cavity contains a reagent, and the sample is optionally drawn into the cavity by capillary force. It should be understood that the use of such cuvette or any similar cuvette is considered to be within the scope of the present invention.

Figure 7A:
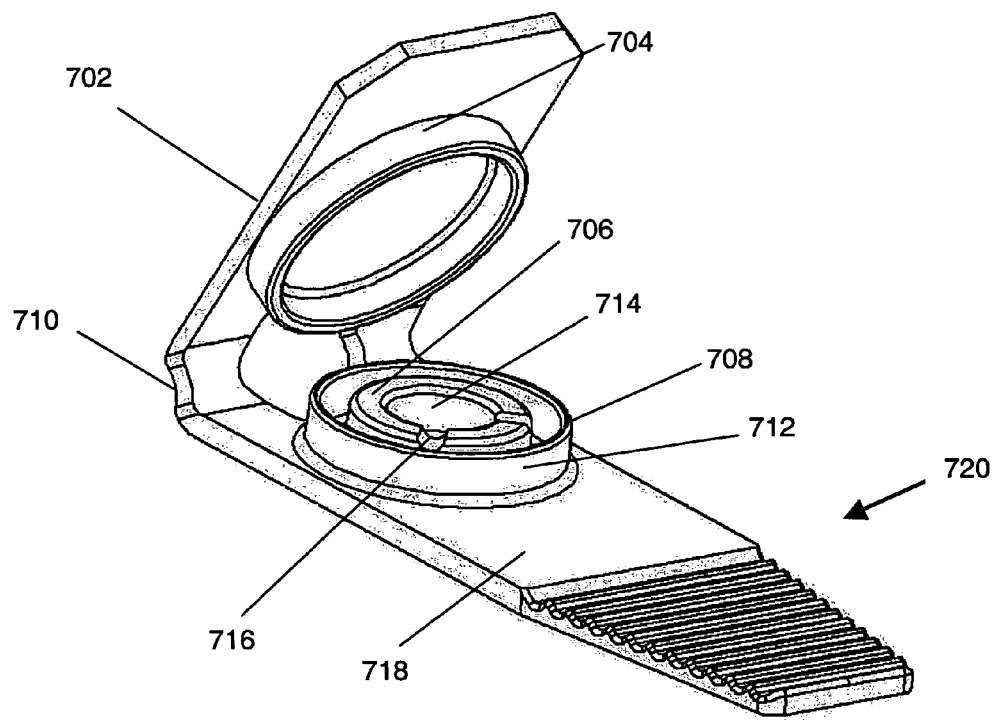
FIG. 7a illustrates an oblique view of the sample tab.
Figure 7B:
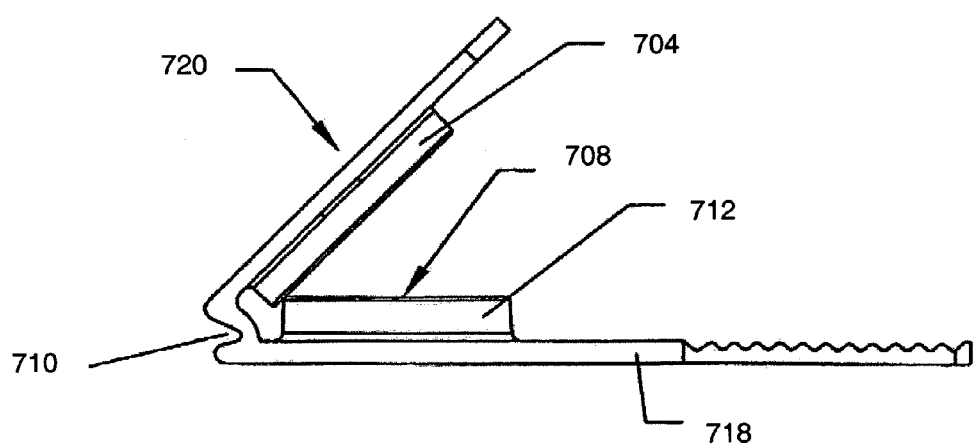
FIG. 7b exhibits a side view of the sample tab.

By "sample tab" it is meant a sample vessel comprising, a base plate having a top surface and a bottom surface, at least a portion of the base plate adapted to permit transmission of EMR therethrough, for example as shown in FIGS. 7a and 7b (720). A well (714) is disposed on the top surface of the base plate (718) for retaining a sample, for example a liquid sample, the well defined by a closed wall (706) extending above the top surface of the base plate, and a cover plate (702), preferably attached to the base plate, for example hingedly attached (e.g. 710) to the base plate, and moveable between an open and a closed position. The closed wall (706) of the sample tab may comprise one or more overflow openings (716), and surrounded by a containment wall (712) so that an overflow ring is defined between the closed wall and the containment wall.

At least a portion of the cover plate permits transmission of EMR therethrough, so that when the cover plate is in the closed position an optical path may be formed through the portion of the base plate that permits transmission of EMR, the well, and the portion of the cover plate that permits transmission of EMR. Alternatively, the sample tab may be configured so that EMR may be reflected off the opposite side of the sample tab, thereby doubling the direct pathlength through a sample present within the sample tab.

The cover plate may be attached to the base plate or may be separate. Further, the sample tab may comprise a locking member that associates with a corresponding mating member, thereby permitting the cover plate to be attached to the base plate. The locking member may comprise, but is not limited to, a circular ring capable of frictionally engaging an outer portion of a containment wall or one or more clips capable of frictionally engaging and attaching the cover plate to the base plate. Although a circular well and an overflow ring are shown in the example, it should be understood the well and overflow section may be of any shape. The locking members may be located on the base plate, cover plate or both the base plate, and the cover plate. Similarly, the associated mating member that receives the locking member may be located on the base plate, cover plate or both the base plate, and the cover plate.

The containment wall may comprise a sealing member on its upper surface (708). The sealing member may be an O-ring, or a pliable material integral with the containment wall. In a preferred embodiment of the present invention, the sample well contains one or more openings or grooves and an overflow ring for collecting excess sample, as closing the cover plate squeezes out excess sample. Preferably, the cover plate is attached to the tab so that the sample proximate the cover plate hinge makes contact with the cover plate first, and as the cover plate closes, excess sample is squeezed out through the two grooves and into the overflow ring. Other features and advantages of the present invention will become apparent from the following detailed description. It should be understood, however, that the detailed description and the specific examples while indicating preferred embodiments of the sample tab are given by way of illustration only. Various designs of sample tabs are described in U.S. patent application Ser. No. 10/042,258, now U.S. Pat. No. 6,841,132; (Publication Number 2002-0110496 A1, Samsoondar; the contents of which are incorporated herein by reference).

By "smoothing" a curve, for example an absorbance spectrum, it is meant applying a mathematical function to the digital data to produce a "continuous spectrum" and thereby reduce the "noise" in the spectrum. Various degrees of smoothing may be applied to a curve. However, loss of analyte signal may be observed as a result of smoothing.

By "second apparatus" it is meant an apparatus that is allowed to function like a first apparatus, whereby the second apparatus need not be calibrated, or need not be calibrated in the same way in which the first apparatus was calibrated (i.e., by conducting a primary calibration). A unique set of samples distinct from the primary calibration set, may be measured on a second apparatus to develop an upgraded primary calibration algorithm, if desired.

By a "standard set of wavelengths" it is meant a set of wavelengths used by all apparatus in conjunction with the apparatus-specific wavelength calibration table, used to generate interpolated absorbances from the measured or actual absorbances. The actual absorbances of a sample tested on an apparatus are measured at wavelengths from the wavelength calibration table, and the actual absorbances may be interpolated and mapped onto the standard set of wavelengths. The primary calibration algorithm(s) is preferably applied to the mapped absorbances, but may be applied to the actual absorbances, particularly when the wavelength calibration table and the standard set of wavelengths are the same. Without wishing to be limiting in any manner, an example of a standard set of wavelengths includes 450 nm to about 300 nm, preferably, from 450 nm to 1100 nm, in increments of 2 nm. However, other wavelength ranges and increments may be used as required, and as would be known by one of skill in the art. The range of the standard set of wavelengths may be derived from the wavelength calibration table, and the increment may be obtained by trial and error. The standard set of wavelengths may also be obtained by establishing a set of wavelengths common to the wavelength calibration tables of both first and second apparatus. Also, the standard set of wavelengths may be obtained by establishing a set of wavelengths that approximate the wavelengths of the wavelength calibration tables of both first and second apparatus.

By a "standard wavelength" it is meant a wavelength from the standard set of wavelengths.

By a "stock Hb-based blood substitute," it is meant a manufactured Hb-based blood substitute that is ready for use, for example, which should not be considered limiting in any way, for infusion into a patient. Hb-based blood substitutes may be used as a quality control material.

By "upgraded primary calibration algorithm" it is meant a calibration algorithm derived from a unique set of samples distinct from the primary calibration set, which are tested on a second apparatus, and the data combined with some or all of the original data from the primary calibration set, to develop one, or more than one, "upgraded primary calibration algorithm."

By "wavelength calibration" it is meant the calibration of a linear diode array detector, charged coupled detector, or any other like device, of a spectrometer, wherein wavelengths are assigned to each pixel in the linear diode array, or charged coupled detector.

By "wavelength calibration table" it is meant a table that provides the actual wavelength corresponding to or assigned to each pixel, which is a result of the wavelength Calibration.

Apparatus

The apparatus of the present invention preferably comprises the following elements:

one or more than one source of electromagnetic radiation (EMR) for illuminating a sample. The source providing EMR characterized as having one or more than one wavelength from about 300 nm to about 2500 nm, or any wavelength therebetween. Preferably, the wavelength is from about 450 nm to about 1100 nm, or any amount therebetween;

one or more than one photodetector for measuring the amount of EMR transmitted through the sample, or reflected from the sample;

an electronic board which optionally contains one or more than one of, an amplifier, an analog-to-digital converter, and a microcontroller, for processing the information received by the one or more photodetectors;

a sample slot in the apparatus for locating the sample vessel; and one or more than one primary calibration algorithm in operative association with the spectroscopic apparatus, wherein the one or more than one calibration algorithm was developed completely on one or more than one other apparatus. One or more than one upgraded primary calibration algorithm (see "Calibration Algorithm Transfer," below) in operative association with the spectroscopic apparatus may also be used within an apparatus of the present invention.

The apparatus can operate in transmission mode or reflectance mode, as will be described in the examples.

Figure 4A:
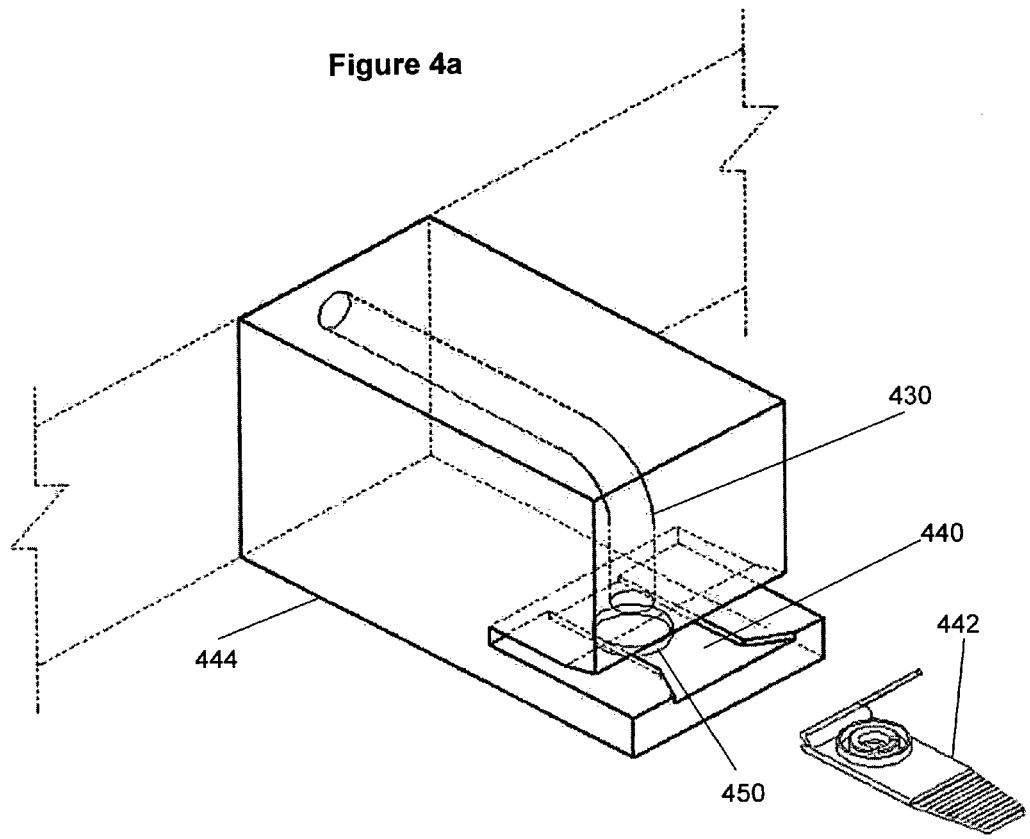
FIG. 4a illustrates oblique views of a sample tab and a sample slot in an spectroscopic apparatus.
Figure 4B:
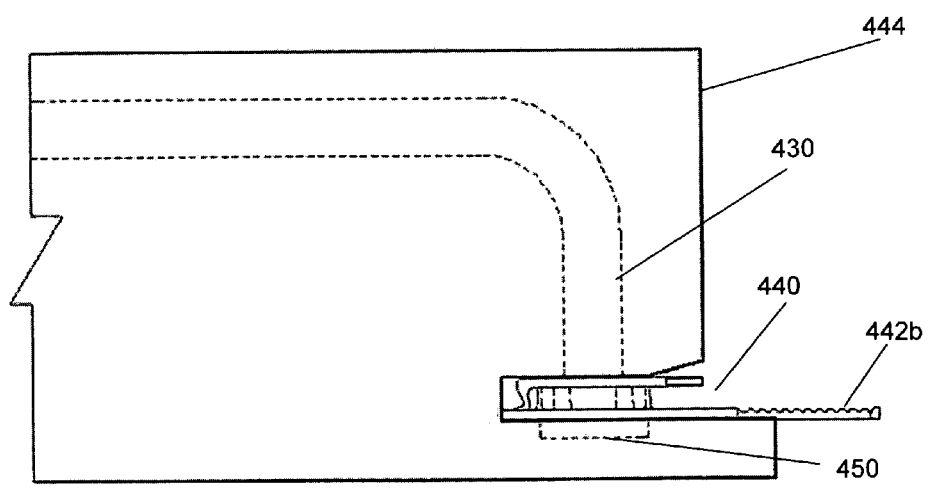
FIG. 4b exhibits a side view of the sample tab inserted in the slot.

Referring now to FIGS. 4*a* and 4*b*, there is shown a sample interface (444) of a spectroscopic apparatus. For the purpose of clarity, the full spectroscopic apparatus is not shown in the figure. A bi-directional bundle of optical fibers 430 may be used, to transmit EMR to a sample place within a suitable holder, for example but not limited to a sample tab (442) and inserted within sample slot (440). Some of the fibers within the bundle 430 receive some of the EMR returning from the sample after EMR is reflected off a reflection member 450. The EMR collected after reflection is channeled to a spectrometer (discussed in more detail with respect to transmission mode and FIGS. 6*a* and 6*b*, below). Processing of EMR after reflection (reflection mode) is the same as the processing of EMR after transmission (transmission mode). Transmission mode is illustrated in FIGS. 5*a*, 5*b*, 6*a* and 6*b*. The sample interface (444) may be separate from the spectroscopic apparatus, and the incident and collection fibers carry the EMR signal to and from an external apparatus. However, as shown in FIGS. 6*a* and 6*b*, the sample interface may also be integral with the spectroscopic apparatus.

Figure 5A:
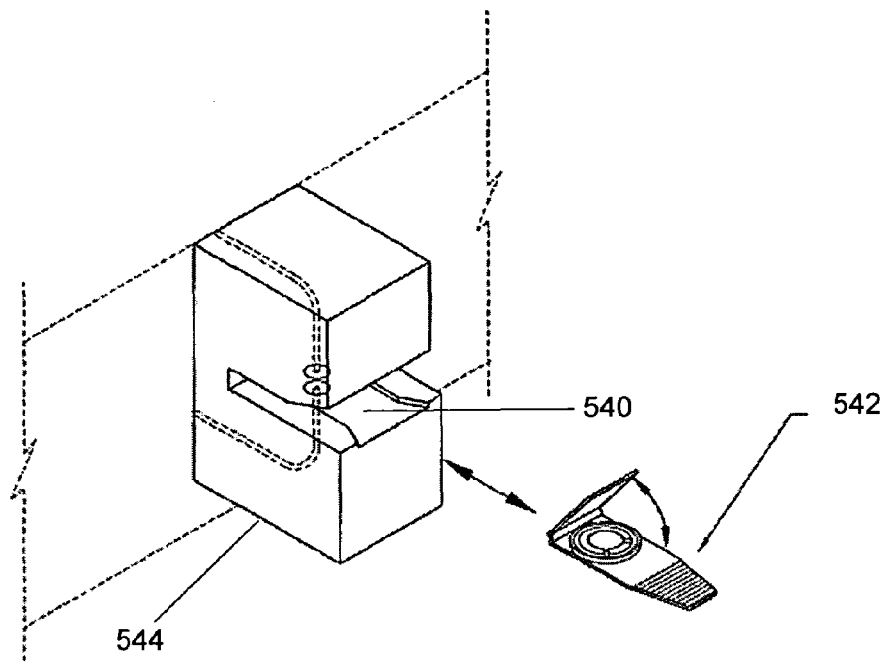
FIG. 5a illustrates oblique views of a sample tab and a slot.
Figure 5B:
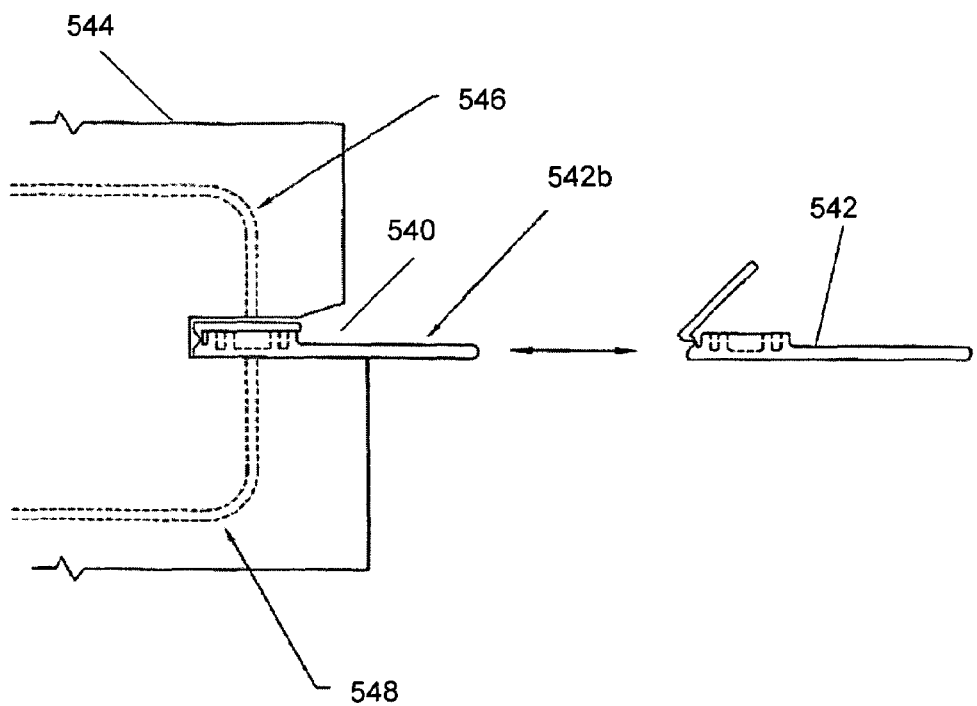
FIG. 5b exhibits a side view of the sample tab inserted in the sample slot.
Figure 6A:
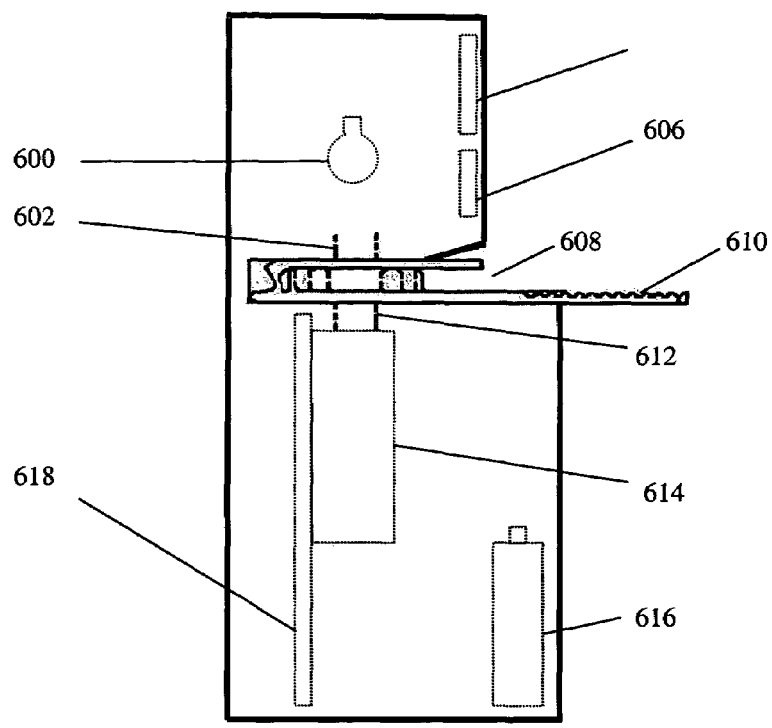
FIG. 6a exhibits a side view of a sample tab inserted in a sample slot.
Figure 6B:
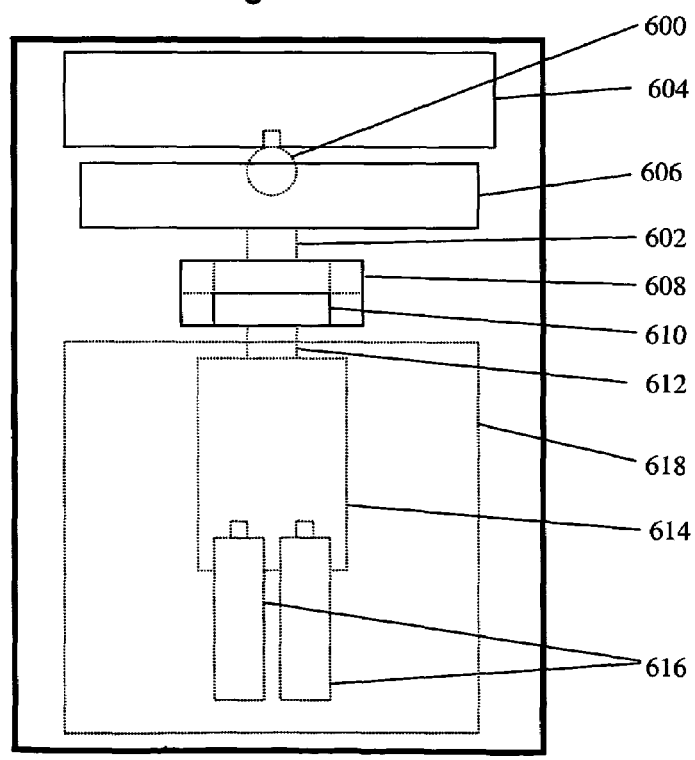
FIG. 6b exhibits a front view of the sample tab inserted into the sample slot.

FIGS. 5*a* and 5*b* show a sample interface (544) of a spectroscopic apparatus that may be used in transmittance mode. For the purpose of clarity, the full spectroscopic apparatus is not shown in the figure. A source of EMR may be provided to the sample (e.g. 542) via an incident optical fiber (548), and the EMR transmitted through the sample collected by a collection optical fiber (546). A sample may be placed within the sample slot (440) using any suitable sample holder, for example a sample tab (542, 542*b*). It should be understood that the incident optical fiber could be 546 and the collection optical fiber could be 548. As indicated above with respect to the reflectance mode, the sample interface (544) may be separate from the spectroscopic apparatus, and the incident and collection fibers carry the EMR signal to and from an external apparatus. However, the sample interface may also be integral with the spectroscopic apparatus (e.g. FIGS. 6*a* and 6*b*).

Referring now to FIG. 6*a* & FIG. 6*b*, there is shown a spectroscopic apparatus (620) comprising any desired source of EMR (600), for example a tungsten lamp. Attenuation of the EMR source may be required to prevent saturation of the detector within the spectrometer (614; detectors 86 are indicated in the spectrometer shown in FIG. 8), and therefore an attenuating device may be placed between the source of EMR and the sample or detector. In the present example the attenuator is an aperture or channel (602) that can be of any appropriate diameter, but the channel could also be a fiber optic of any length or diameter, or other attenuating device, for example a filter or other device known to one of skill in the art that controls the amount of incident EMR reaching the sample slot (608).

A reference measurement can be taken before or after a sample measurement, or the reference measurement can be stored and reused any number of times. By inserting an opaque member in the sample slot (608), a dark current measurement can be made. By "dark current" it is meant the detector response when the detector is not exposed to EMR. Subtraction of a dark current measurement is optional, and no dark current measurement is required.

The EMR emerging from the sample slot (608) can enter the spectrometer (614), through channel 612. Channel 612, is shown as an aperture between the sample tab and the spectrometer, but the channel could be a fiber optic of any length, as shown in FIGS. 4 (430), % (546 or 548) or 8 (612).

Figure 8:
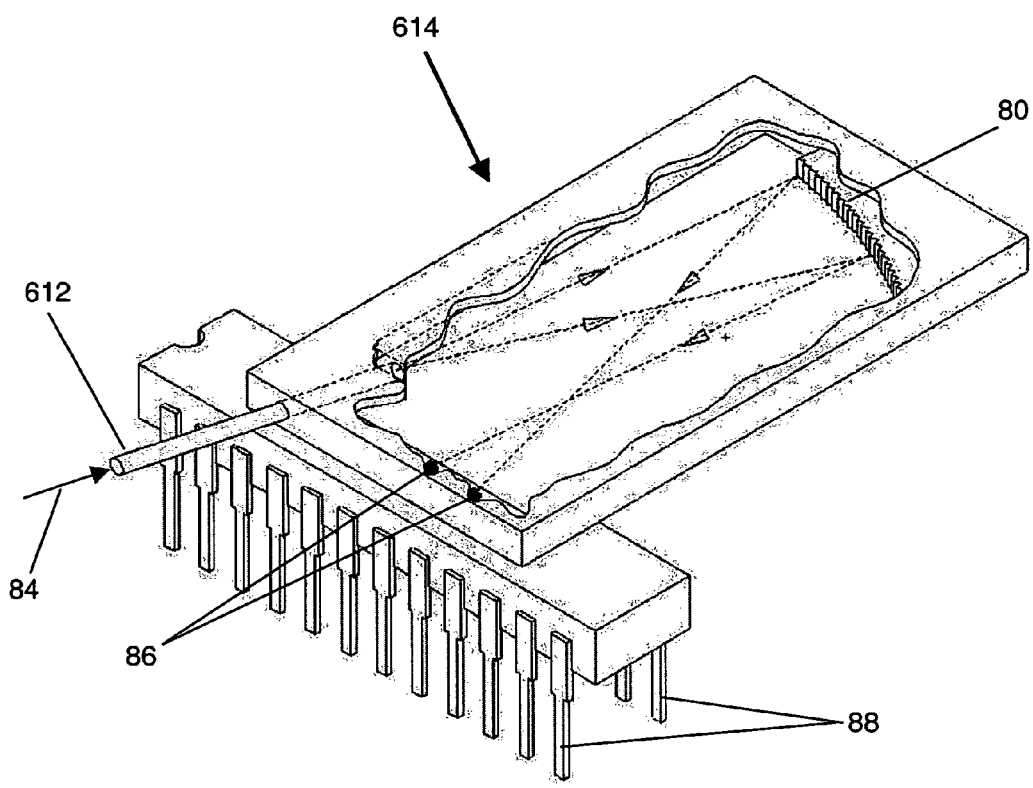
FIG. 8 shows a spectrometer 614 (with a cut-out view) used in the preferred embodiment. For simplicity, only two photodiodes are shown.

The spectrometer, for example as shown in FIG. 8, may comprise a diffraction grating 80. Either a transmission or reflection grating may be used. In the example shown in FIG. 8, the diffraction grating 80 is a reflection grating. A grating is a dispersing element, which separates out the EMR component by wavelengths. In the preferred embodiment, the detector in spectrometer (614) is an array of photodiodes (e.g. 86 in FIG. 8; for simplicity, only two diodes are shown in this figure), but the use of a single detector instead of an array of detectors may also be used. LED's may be used as a source of EMR, and with the use of LED's, a grating may not be required. For example, which should not be considered limiting in any way, a single detector could be used when the source of EMR (600) is one or more LED's.

The power source may be any suitable source, for example, which is not to be considered limiting, the power source in FIG. 6 is shown as comprising two batteries (616). However, the apparatus may also be powered by an external power source, for example alternating current from a wall outlet.

The electronic signal received by the spectrometer is proportional to the time that the detector integrates the optical signal. The electronic signal may be amplified by analog electronic amplifiers (not shown) and converted to a digital signal by an analog-to-digital converter or ADC (also not shown).

Referring again to FIG. 8, there is shown an example of a spectrometer that maybe used in accordance with the present invention. EMR emerging from the sample (84) impinges upon a reflection grating (80), and is dispersed into its component wavelengths. The dispersed EMR then impinges upon an array of diodes (e.g. 86), so each diode represents a pixel. The array has a known pixel dispersion, which would allow the assignment of wavelengths for each pixel. The array of pixels represents a range of wavelengths, for example the wavelength range may be about 450 nanometers to about 800 nanometers, with a pixel dispersion of about 3 nanometers per pixel. An example of a suitable spectrometer is produced by MicroParts, Germany, and contains 256 diodes. For simplicity, only two diodes (86) are shown in FIG. 8. It should be understood that any number of pixels are within the scope of the present invention. Wavelength calibration (and a Standard Set of Wavelengths) of spectrometers is discussed in detail in U.S. Pat. No. 6,651,015 (Samsoondar; which is incorporated herein by reference. The use of any spectrometer is considered to be within the scope of the present invention.

Also shown in FIG. 8, is output from the diode array (88) that may be coupled to the electronic board (618 shown in FIGS. 6a and 6b). The electronic board (618) may also comprise an amplifier, an analog-to-digital converter, and a microcontroller, although these elements are not shown in FIG. 6a and 6b.

As shown in FIGS. 6a and 6b, a sample tab (610) may be inserted in sample slot (608). Commands can be executed from a keyboard or keypad (606), and data, for example results, which should not be considered limiting in any way, may be displayed on a monitor or screen (604). It should be understood that the use of one or more switches, buttons, or keys are preferred to a keyboard or keypad, for a hand-held apparatus, and all are considered to be within the scope of the present invention. It should also be understood that use of a host computer is also considered to be within the scope of the present invention. Communication ports, which are not shown, are optional.

Appropriate shielding of the sample slot and detectors from room light may also be desired, but the extent of shielding depends on the analyte or parameter measured, and the use of dark current measurement. It should be understood that the apparatus could be oriented on any side, particularly with the top and bottom switched, i.e., with the source of EMR shown below the sample, instead of above as is FIGS. 6a and FIG. 6b.

Absorbance is calculated by the microcontroller, which is installed (but not shown) on electronic board 618 as:

$$\text{Absorbance}_i = \log\{(RL_i - RD_i)/(SL_i - SD_i)\} + \log(ITS/ITR)$$

where:
- Absorbance$_i$=Absorbance at pixel i;
- $RL_i$ is Reference Light$_i$=Reference pixel i readings;
- $RD_i$ is Reference Dark$_i$=Reference pixel i readings;
- $Sl_i$ is Sample Light$_i$=Sample pixel i readings;
- $Sd_i$ is Sample Dark$_i$=Sample pixel i readings;
- ITS=Integration time for sample measurement;
- ITR=Integration time for reference measurement; and
- i=the particular pixel (wavelength) in the array of detectors The method of the present invention requires that one or more than one calibration algorithm for one or more analytes is installed in the spectroscopic apparatus (this may involve the process of calibration algorithm transfer), for example which is not to be considered limiting, the one or more than one calibration algorithm may be installed within the microcontroller which is integrated in the electronic board (618). However, one or more than one calibration algorithm could be installed in any form of non-volatile memory, for example, which should not be considered limiting in any way, ROM, EPROM, EEPROM (electronically erasable programmable read only memory), CD, diskette, or memory card. By installing one or more than one calibration algorithm in an apparatus by any means, the one or more than one calibration algorithm is brought into operative association with the apparatus.

The apparatus may comprise a sample slot (e.g. 540, FIG. 5) for receiving a sample vessel (e.g. 542, FIG. 5), for testing. By "sample slot" it is meant an opening through which the sample vessel is to be placed, or a groove or channel or slit into which the sample vessel fits. It should be understood that the slot could be oriented in any direction, but it is shown in FIGS. 5 and 6 as a horizontal slot, such that the EMR travels in the vertical direction. Alternate configurations include spectroscopic apparatus comprising a vertical sample slot, for receiving a sample vessel, for example a cuvette. In this configuration, the EMR passes though the sample in the horizontal direction.

As shown in FIGS. 5 and 6, the sample slot may be adapted to allow EMR to enter either a top side of the slot housing the sample vessel, and the transmitted EMR collected at the bottom side of the slot, or visa versa, with the incident EMR entering the bottom side of the slot, and exiting from the top side. The slot may also be adapted to allow EMR to enter the top side of the slot housing the sample vessel, where the transmitted EMR is reflected off a reflective surface or reflective member (e.g. 450; FIGS. 4a and 4b) located at either the bottom side of the slot. It should be understood that the transmitted EMR could be reflected off a reflective surface located on the side of the sample vessel at or near the back side of the slot, and the reflected EMR is collected at the top side of the slot.

The sample vessel may optionally contain one or more reagents, and the sample vessel may be any suitable vessel, including a cuvette or a sample tab, that may optionally contain one or more reagents.

Sample Tab

A non-limiting example of a sample vessel is a sample tab. The sample slot is designed to accept the sample tab in any suitable direction, for example a horizontal direction. A horizontal direction may be preferred when the sample is whole blood, since when whole blood is allowed to settle red blood cells tend to precipitate. In this case, in order for the red blood cells to remain in the path of the EMR, the EMR should travel in the vertical direction. However, any configuration of the sample slot is considered to be within the scope of the present invention. The sample vessel may also be a cuvette designed to draw in a sample by capillary action, and may optionally contain one or more reagents.

The sample tab may comprise a base plate with a sample well and a cover, wherein at least a portion of the base plate and at least a portion of the cover, is adapted to permit transmission of EMR therethrough. Alternatively, the sample tab may comprise a base plate with a sample well and a cover, wherein at least a portion of the base plate is adapted to permit transmission of EMR through the sample, and at least a portion of the cover is adapted to reflect EMR emerging from the sample, and wherein the reflected EMR is allowed to traverse the sample before leaving the sample tab at the base plate, or wherein at least a portion of the cover is adapted to permit transmission of EMR through the sample, and at least a portion of the base plate is adapted to reflect EMR emerging from the sample, and wherein the reflected EMR is allowed to traverse the sample before leaving the sample tab at the cover. According to an aspect of the present invention, there is provided a sample tab for retaining a sample for testing. It should be understood that the sample tab is used as an example of a sample vessel, and should not be considered limiting in any way.

In use, a sample is retained in the well between the base plate and the cover plate of the sample tab so that electromagnetic radiation may pass through the base plate, through a sample in the well, and the cover plate. However, it is within the scope of the present invention that the radiation beam may travel though the sample, and be reflected off either the base plate or cover plate thereby doubling the path length of the radiation beam. By doubling the path length, a reduced volume of sample may be used during analysis. Either the base plate or the cover plate may have a reflective surface, or may be made of, reflective material. As an alternative, the sample tab may be made out of a transparent or translucent material, and still used in reflection mode as shown in FIGS. 4a and 4b. In this case the reflecting member (450) placed below the sample slot (440) may comprise for example but not limited to, a ceramic coating, barium sulfate, SPECTRALON™, SPECTRAFLECT™, or DURAFLECT.™

Referring now to FIGS. 7a and 7b, there is shown an aspect of an embodiment of the sample tab, which should not be considered limiting in any way. Sample tab (720) comprises base plate (718), cover plate (702) and sample well (714) defined by closed wall (706). Sample well (714) may be of any volume required, for example, but not limited to, a size sufficient to allow a drop of blood to fill the well, preferably with some excess. For example, which is not to be considered limiting, the well may be circular, as shown in FIG. 7a and 7b, and comprises dimensions of about 4 mm in diameter and about 2 mm in depth.

Overflow openings or grooves (716) in closed wall (706) allow excess sample to flow out of sample well (714) when cover plate (702) is closed over sample well (714) and base plate (718). A second wall, such as, but not limited to, a containment wall (712) may be employed to retain the sample that overflows sample well (714), into an overflow ring (circular groove between wall 706 and wall 712) to prevent leakage of fluid from the sample tab, while permitting a sample of sufficient volume to fill the well. In this regard, the vertical height of containment wall (712) is less than or equal to the height of closed wall (706) defining sample well (714). More preferably it is equal to the height of closed wall (706) defining sample well (714). Cover plate (702) is preferably attached to base plate (718) by a hinge (710) or other suitable attachment means known in the art. However, a non-hinged cover plate may also be used, where the cover plate may be snapped on to the base plate.

The sample tab may be manufactured from any suitable material known in the art, for example, but not limited to, a transparent, translucent material, such as glass, plastic or a combination thereof, or a reflective material in parts. If the base plate and cover plate are transparent or translucent, then it is preferred that the base plate, and cover plate comprise a transparent or translucent plastic, such as but not limited to polypropylene, polycarbonate, polyethylene, or polystyrene, however, a glass plate may also be used. If either of the base plate or cover plate is reflective, then a reflective material, for example but not limited to a ceramic coating, barium sulfate, SPECTRALON™, SPECTRAFLECT™, or DURAFLECT™ may be used for one of the base or cover plates.

Optionally, the sample tab may comprise a locking member to lock cover plate (702) to the base plate (718). The locking member may comprise a portion of the cover plate, base plate or both. Further, the locking member may reversibly or irreversibly lock the cover to the base plate. Any locking member known in the art may be employed with the sample tab of the present invention, for example, but not limited to those as shown in U.S. patent application Ser. No. 10/042,258, now U.S. Pat. No. 6,841,132 (Publication Number 2002-0110496 A1; Samsoondar; the contents of which are incorporated by reference). The use of a containment wall ensures that the sample is retained within the sample tab and reduces contamination between samples. Furthermore, by locking the cover plate of the sample tab in a closed position, the sample tab may be readily disposed of after use without sample leakage, or the sample tab may be used in a vertical position, for example within a cuvette holder adapted for use with in spectroscopic apparatus.

Also shown is a locking member (704) which permits cover plate (702) to be fastened to base plate (718). In this example, the locking member (704) comprises a circular ring, capable of frictionally engaging the containment wall (712), thereby reversibly attaching cover plate (702) to base plate (718), preventing the escape of a sample from the sample tab.

When the cover plate is closed over the well, and attached to the base plate, it is preferred that the top surface (708) of the containment wall (712) seals against the lower surface of the cover slip. However, the locking member may also be used to help seal the sample within the sample tab should any leakage occur past the containment wall.

According to another aspect of the sample tab, the absorbance can be calculated from reflectance instead of transmittance. In the case of reflectance, either the base plate or the cover plate may have a reflective surface or may be made of reflective material. Such a reflective surface or material could include any suitable reflective coating, for example, but not limited to, a ceramic coating, barium sulfate, SPECTRALON™, SPECTRAFLECT™, or DURAFLECT™.

Wavelength Calibration

Spectrometers should be calibrated, if wavelengths are used in the calibration algorithms, instead of pixel numbers. In order to facilitate calibration algorithm transfer, wavelength calibration of the spectrometer is required. Several methods of wavelength calibration are given below as example only, and should not be considered limiting in any way:

Method 1:

A laser of known wavelength or EMR transmitted through a band-pass filter of know wavelength, is projected onto any pixel in a linear diode array. It should be understood that the EMR should not be restricted to a laser or a band-pass filter, and other sources of monochromatic EMR may be used. It should also be understood that the EMR could impinge upon more that one pixel, and that the relative position of peak intensity of the EMR may be determined mathematically by processes known to those skilled in the art. Further, the peak intensity may be positioned between any two pixels. The targeted pixel is preferably towards one end of the spectrum. A second laser of known wavelength or EMR transmitted through a second band-pass filter of known wavelength that is preferably projected towards the other end of the spectrum may be used and the pixel on which the beam is projected onto is identified. Since the number of pixels is known, one can determine the pixeldispersion. With the two known wavelengths and their corresponding pixels, and the pixeldispersion, one can generate a wavelength calibration table i.e., a table providing the discrete wavelength that is assigned to each pixel in the linear diode array.

The absorbances at the wavelengths from the wavelength calibration table from one or more apparatus, can subsequently be interpolated and mapped unto a standard set of wavelengths. The absorbances at the two actual wavelengths that are on either side of the standard wavelength may be interpolated to produce an absorbance at a standard wavelength. This process may be repeated for each standard wavelength. This is, the preferred method for making the wavelengths provided by different apparatus, appear similar. Photometric accuracy depends in part on wavelength accuracy, and the prediction accuracy for an analyte concentration depends upon the photometric accuracy of the apparatus. In this respect, a qualitative method for an analyte where a yes/no answer is all that is desired does not require the same level of wavelength accuracy as a quantitative method for the same analyte. Furthermore, the calibration algorithm can be developed with more robustness by including data from one or more primary calibrators, measured on the first apparatus and one or more similar apparatus.

In this method of wavelength calibration, the first wavelength does not have to be projected upon the same pixel in the linear diode array of each apparatus, since the absorbances could be interpolated and mapped unto a standard set of wavelengths. The wavelength of a second laser or second band-pass filter is preferably chosen so that the beam of EMR is projected towards the other end of the linear diode array. It is preferred that the laser or band-pass filter be selected so that the beam of EMR is not projected too close to the end pixels in the linear diode array, if the resulting absorbances at the end pixels are noisy. It is also preferred that a bandpass filter is a narrow bandpass filter.

Method 2:

A second method to generate a wavelength calibration table is to project the first beam onto the same pixel of each linear diode array. When this method is used to generate a wavelength calibration table, the pixeldispersion is predetermined using two beams of different wavelengths, as described above. The pixeldispersion may be determined from a single spectrometer, but preferably the average value should be obtained from more than one like spectrometer. When the same pixeldispersion is used by each apparatus and the first beam is projected onto the same pixel number within each like linear diode array, the wavelength calibration table for each apparatus would be the same, and hence the wavelength calibration table may be used as the standard set of wavelengths. Consequently interpolation and mapping of absorbances to a standard set of wavelengths would automatically be eliminated. A second beam may be used to validate wavelength accuracy.

Method 3:

A third method to generate a wavelength calibration table is like the second method except that the first beam may be projected onto any pixel of the linear diode array. When the pixel number that the first beam is projected onto, is different in different apparatus, the pixel numbers assigned to a specific wavelength in the wavelength calibration table of the different apparatus will differ. In this case, software may be used to produce a standard set of wavelengths as follows:
  (i) Establish a set of wavelengths common to the wavelength calibration table of the different apparatus.
  (ii) Select a range of wavelengths of the standard set of wavelengths, the range of wavelengths having wavelengths belonging to the standard set of wavelength.

It should be understood that the wavelength calibration table obtained from different apparatus as described in above third method may be such that a pixel number from different apparatus may not be assigned the same wavelength. It should also be understood that the first pixel may be an approximation to a pixel number and also the first pixels from different apparatus may be approximated to be the same pixel, and that the approximations tolerated depends on the prediction accuracy required for the primary calibration algorithms. In other words, the identification of the first pixel may be incorrect. An incorrect identification can be tolerated provided that the incorrectly identified pixel is within less than or equal to about +/−N pixel, where N is the number of pixels that encompass a range of wavelength. Fore example, if the pixel dispersion is 2 nm and if the tolerated error is +/−10 nm, then the incorrectly identified pixel must be no more than 5 pixels away on either side of the actual pixel on which the beam impinged. Different levels of error may be tolerated typically, but not limited to +/−2 nm to +/−20 nm and more preferably from +/−2 nm to +/−10 nm. Selection of a wavelength calibration method depends on the required prediction accuracy of the primary calibration algorithms.

Calibration Algorithm Transfer

Another aspect of the present invention is calibration algorithm transfer. One or more than one calibration algorithm in operative association with the spectroscopic apparatus, for example, installed in the microcontroller in the electronics board (618) shown in FIGS. 6a and 6b is used for determining the presence or concentration of one or more than one analyte in a sample. It should be understood that the one or more than one calibration algorithm could be installed in any form of non-volatile memory, for example, which should not be considered limiting in any way, ROM, EPROM, EEPROM (electronically erasable programmable read only memory), CD, diskette, or memory card. The one or more calibration algorithms were previously developed on one or more first apparatus by the process of primary calibration, and the one or more calibration algorithms were transferred to other apparatus, referred to as second apparatus. Calibration algorithm transfer is discussed in U.S. Pat. No. 6,651,015 (Samsoondar; which is incorporated herein by reference).

In the preferred embodiment, a primary calibration algorithm is developed completely on one or more than one other apparatus, and simply installed in the apparatus of the present invention; no adjustment of the constants or coefficients of the primary calibration algorithm is made in the preferred embodiment. However, it should be understood that a calibration algorithm could also be derived using a set of unique samples distinct from those used in the primary calibration set, which are tested on a second apparatus, and the data combined with some or all of the original data from the primary calibration set, to develop one, or more than one, "upgraded primary calibration algorithm." It should be understood that the use of one or more upgraded primary calibration algorithm is also considered to be within the scope of the present invention. Upgraded primary calibration algorithms are also discussed in U.S. Pat. No. 6,651,015 (Samsoondar; which are incorporated herein by reference).

For greater accuracy of a predicted value of an analyte concentration, absorbances that are measured at actual wavelengths of the second apparatus, could be mapped to a standard wavelength of a set of standard wavelengths, by interpolating absorbances at actual wavelengths that encompass the standard wavelength. Mapping of absorbances and interpolation of absorbances are also discussed in U.S. Pat. No. 6,651,015 (Samsoondar; the contents of which are incorporated herein by reference).

After calibration algorithm transfer, "photometric correction" or absorbance correction could also be performed, depending on the required accuracy of the analyte tested for. Photometric correction or absorbance correction is also discussed in U.S. Pat. No. 6,651,015 (Samsoondar; the contents of which are incorporated herein by reference).

It should be understood that the terms spectrometer and spectrophotometer are sometimes used interchangeably, and the inventor does not make any distinction between the two terms.

Hemoglobin in Body Fluids

The accuracy of measurement of Hb as an indicator of hemolysis, depends upon several factors, for example, which is not to be considered limiting:

1) The Hb species selected as the indicator of hemolysis;
2) The constituents of each sample in the primary calibration set used to develop the primary calibration algorithm; and
3) The Hb species included in the reference value for the indicator of hemolysis.

U.S. Pat. No. 6,268,910 B1, U.S. Pat. No. 5,846,492, WO-98/39634, and WO-97/47972 describe calibration algorithms for Hb, wherein Hb is used as an indicator of hemolysis. However, none of these documents indicate the Hb species used as an indicator of hemolysis, nor is there any suggestion that Total-Hb is used as the indicator of hemolysis.

It should be appreciated by those of skill in the art, that although a primary calibration algorithm is developed for a particular analyte using accurate estimates of the reference values for the analyte, other analytes or substances that are present in a sample may introduce errors in the predicted values for the analyte. This applies particularly to the predicted values of an indicator of hemolysis, where the Hb could exist as several Hb species, and these Hb species need to be accounted for in the primary calibration algorithm. For example, the indicator of hemolysis could be Total-Hb, and the reference measurement made using standard methods, for example but not limited to, the cyanMet-Hb reference method for Total-Hb measurement (Tietz Textbook of Clinical Chemistry, $3^{nd}$ Ed, 1999, p1673-1674). If the Total-Hb present in the primary calibration samples is not comprised of a suitable variation of the Hb species, the Total-Hb predicted value for a sample with a high proportion of Met-Hb, could be underestimated significantly.

The required accuracy of measurement of the indicator of hemolysis depends on the application of the indicator of hemolysis. Any substance present within a red blood cell (RBC) and not present in the plasma that surrounds the RBC, can be used as an indicator of hemolysis, as hemolysis liberates substances contained within the RBC's into the plasma or serum. Hb is an example of a substance contained inside the RBC's, and is only present in serum and plasma if hemolysis has occurred.

Hemolysis can occur in vitro, for example if the sample was handled roughly, or hemolysis can occur in vivo, for example in patients with fragile RBC membrane or in patients with prosthetic heart valves. Therefore, for accurately measuring an indicator of hemolysis it is desirable to determine:

1) the full extent of a combination of in vivo and in vitro hemolysis;
2) the true level of hemolysis, for example to understand by how much the concentration of a substance like potassium can become artificially elevated in serum or plasma, due to in vitro hemolysis (potassium is another example of a substance released from hemolyzed RBC's, as its concentration within the RBC's is about 25 times that of plasma); and
3) the increase in absorbance of the serum or plasma due to the release of hemoglobin, in an effort to understand how and to what extent the artificially increased absorbance due to Hb, affects spectroscopic assays for other analytes.

Total Hb is a sensitive indicator of hemolysis, and provides a good estimate of the extent of hemolysis. The composition of normal Hb in arterial blood is about 95% oxy-Hb, about 1% Met-Hb, about 2% carboxy-Hb, and about 2% deoxy-Hb, measured in an arterial blood sample by CO-oximetry. The art of CO-oximetry is well known and deals with the measurement of Hemoglobin species in whole blood: Oxy-Hb, Deoxy-Hb (or reduced-Hb), Met-Hb, and Carboxy-Hb. The proportion of the Hb species seen in most serum and plasma samples with hemolysis, is similar to that described for arterial blood, even though the serum and plasma is usually obtained from a venous blood sample. Although the percentage of Oxy-Hb of Total-Hb, called the Hb oxygen saturation, is usually much higher in an arterial blood sample, compared to that of a venous blood sample (because of the increase in Deoxy-Hb in venous blood), the increase level of Oxy-Hb in a venous sample (serum or plasma) is due to exposure of the sample to air, which contains 20% oxygen (i.e., a partial pressure of oxygen of 152 mm Hg, 20% of 760 mm Hg). Therefore, Oxy-Hb is another sensitive indicator of hemolysis, especially in blood samples with normal Hb species.

Figure 3:
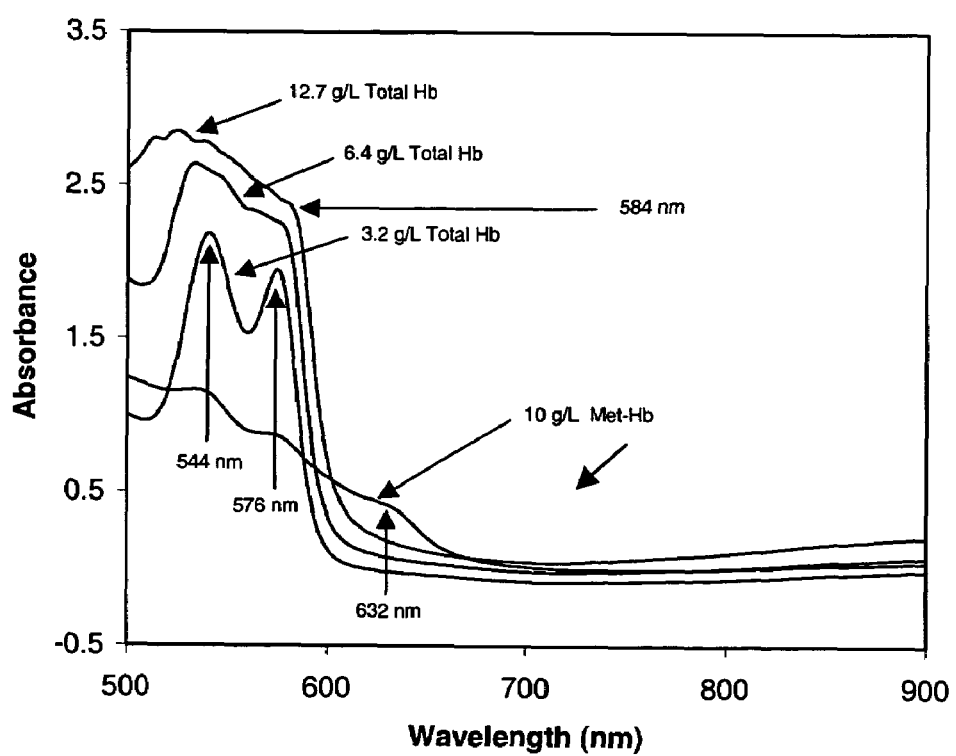
FIG. 3 shows a graphic representation of the absorbance spectra of three different concentrations of total Hb, from the same pool. The total Hb was allowed to become partly oxidized to produce Met-Hb, which is also shown.

An increase in Met-Hb within a sample is shown in FIG. 3, but the fraction of the Total-Hb that is in the Met-Hb form is unknown. The Met-Hb shown in FIG. 3 was created by spontaneous oxidation of Hb. The blood donor used to provide the hemolysate with absorbance spectra shown in both FIG. 3 is the same, and the absorbance spectra of the fresh hemolysate, made on different days, were indistinguishable. Although this discussion is more directed to hemolysis in serum and plasma, the same discussion could be applied to any body fluids, including whole blood.

Figure 2:
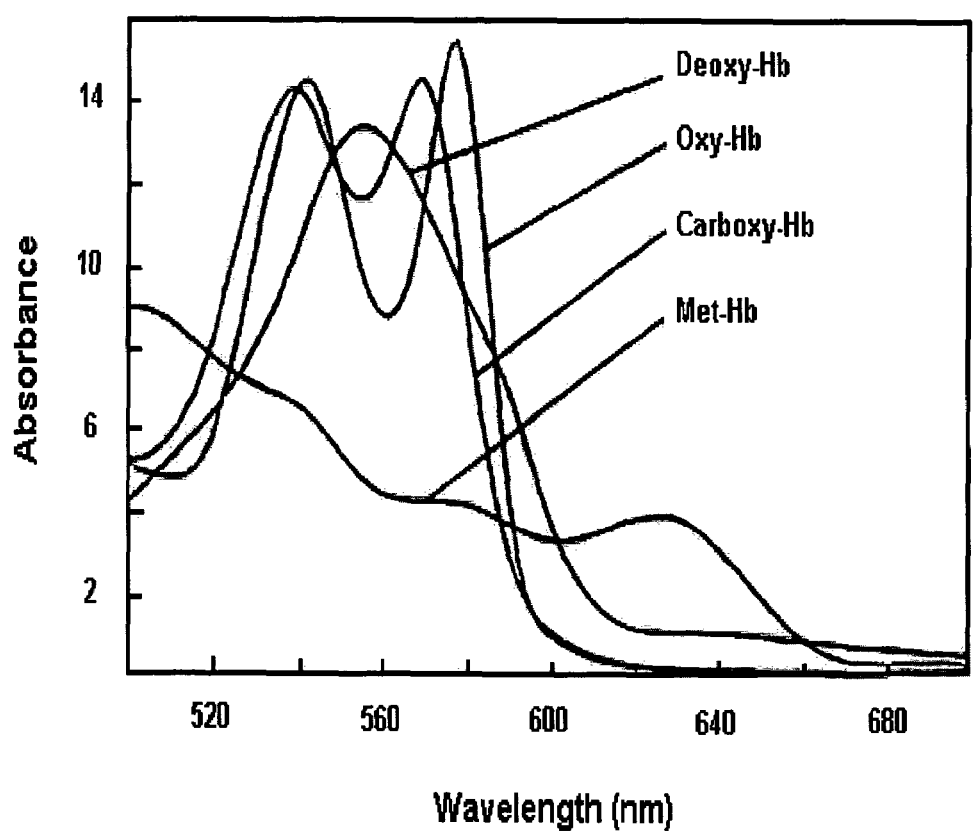
FIG. 2 shows a graphic representation of the absorbance spectra of four different hemoglobin species, as shown, in the wavelength range of 500-700 nm plotted on the x-axis, and absorbance of the same concentration of each specie (equivalent to extinction coefficient) on the y-axis.

The absorbance spectra for Oxy-Hb, Deoxy-Hb and Carboxy-Hb are very similar in the region from about 576 nm to 700 nm (particularly from about 590 nm to about 610 nm, as shown in FIG. 2), compared with absorbance of Met-Hb, (which is much lower) in the same wavelength region. Met-Hb also exhibits a characteristic absorbance peak at about 632 nm. Therefore, if a calibration algorithm for Total-Hb is developed, for example, using reference values that are estimates of Total-Hb, comprising about 95% Oxy-Hb, large quantities of Deoxy-Hb and Carboxy-Hb in a sample would be included in the measurement of Total-Hb. However, the absorbance of Met-Hb is low in the 576 nm to 700 nm region, which could result in a significant underestimation of Total-Hb compared to the reference measurement of the Total-Hb. In this case, the predicted values derived from the calibration for Total-Hb as the indicator of hemolysis, would be more reflective of the "Total-Hb minus Met-Hb." In this example, the indicator of hemolysis may be more appropriately called, "Total-Hb minus Met-Hb."

Figure 9:
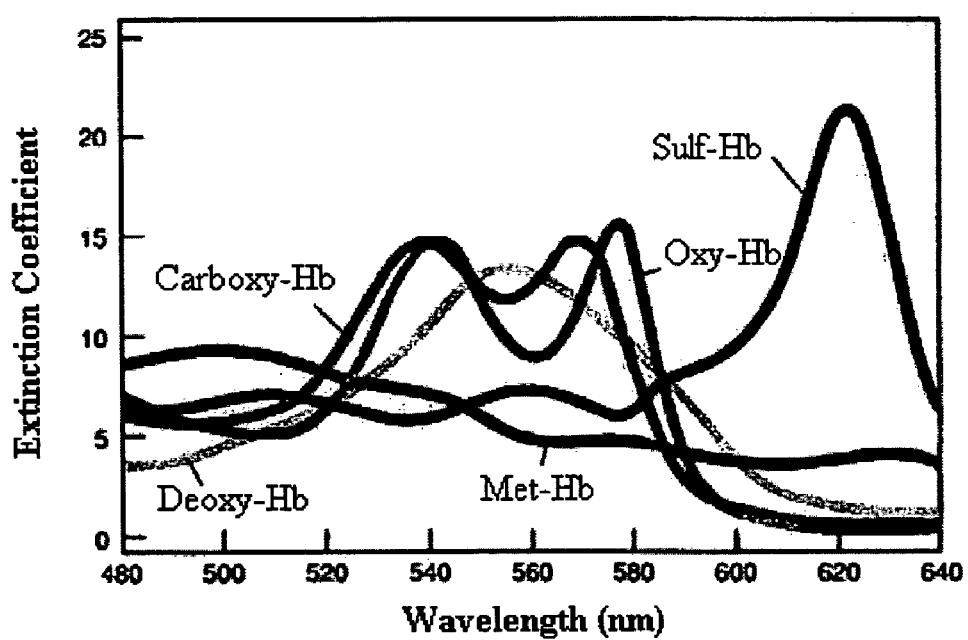
FIG. 9 shows a graphic representation of the absorbance spectra of five different hemoglobin species, as shown, in the wavelength range of 480-640 nm plotted on the x-axis, and extinction coefficient plotted on the y-axis.

In addition to the four Hb species shown in FIG. 1 and FIG. 2, a fifth Hb species, Sulf-Hemoglobin (Sulf-Hb), is shown in FIG. 9 (see Clin. Chem. News 1990; 16(1) pp11-12). Sulf-Hb is greenish in color and contains sulfur, and iron in the ferric form. Met-Hb also contains iron in the ferric form, but the iron in Oxy-Hb, Deoxy-Hb, and Carboxy-Hb, is in the ferrous form. The large absorbance of Sulf-Hb, which peaks at about 620 nm (FIG. 9), may be used to obtain a calibration algorithm that predicts Sulf-Hb. Use of certain drugs, for example, which should not be considered limiting in any way, sulfonamides, phenacetin, acetanilide, phenazopyridine, dapsone, and metoclopramide, are associated with an accumulation of Sulf-Hb (Wu, C. et al. Clin. Chem. 1997; 43(1) pp 162-166).

In the example where the Oxy-Hb is about 95% of all the Hb species, the reference values of Oxy-Hb can be used as an estimate of Total-Hb. A sample of known Oxy-Hb concentration where the Oxy-Hb fraction is about 95% of the Total-Hb, can be considered to have a total Hb concentration of same value as the Oxy-Hb concentration. Similarly, a sample of known Total-Hb concentration that comprises about 95% Oxy-Hb, can be considered to have an Oxy-Hb concentration of the same value as the Total-Hb concentration. A sample of known "Oxy-Hb plus Deoxy-Hb" concentration where the "Oxy-Hb plus Deoxy-Hb" fraction is about 95% of the Total-Hb, can be considered to have a Total-Hb concentration of same value as the "Oxy-Hb plus Deoxy-Hb" concentration. Similarly, a sample of known Total-Hb concentration that comprises about 95% "Oxy-Hb plus Deoxy-Hb," can be considered to have an "Oxy-Hb plus Deoxy-Hb" concentration of the same value as the Total-Hb concentration. It should be understood that the term "Oxy-Hb" and "Oxy-Hb plus Deoxy-Hb" can be used interchangeable when the sample is exposed to atmospheric oxygen, because the Deoxy-Hb quickly absorbs oxygen and becomes converted to Oxy-Hb. The predicted values of Oxy-Hb or "Oxy-Hb plus Deoxy-Hb," will not be significantly affected by Met-Hb, if affected at all, but the predicted values of Oxy-Hb or "Oxy-Hb plus Deoxy-Hb" will not be a reliable estimate of hemolysis or Total-Hb, since most of the Met-Hb will not be measured.

Although the method of measuring Hb discussed above is with respect to contamination of a body fluid with Hb, or hemolysis in plasma and serum, it should be understood that measurement of Hb in whole blood is considered to be within the scope of the present invention. The only difference between Hb in whole blood and Hb in serum or plasma is the Hb concentration and the light scattering effect of RBC's. INTRALIPID particles may be added to some samples in the primary calibration sets for Hb in serum or plasma, to increase the light scattering effect typically associated with RBC's. It should be understood that body fluids are not limited to humans, and body fluids from other species, for example animals, are within the scope of the present invention.

Therefore, an aspect of one of the methods of the present invention is to overcome the underestimation of Total-Hb in the presence of large quantities of Met-Hb as follows:

Method 1: Add Met-Hb to the primary calibration set, and include the Met-Hb in the reference values of Total-Hb for the development of a calibration algorithm; or Method 2: Add Met-Hb in the primary calibration set, and do not include the Met-Hb in the reference value for Hb during development of the primary calibration algorithm.

In Method 1, the calibration algorithm for Total-Hb could partly include Met-Hb in the predicted Total-Hb results.

In Method 2, the calibration algorithm would predict "Total-Hb minus Met-Hb," and any Met-Hb in a sample would be ignored Referring again to Method 2, a separate primary calibration algorithm may be developed for Met-Hb for determination of Met-Hb in a sample, to flag samples with Met-Hb that exceed a predetermined value, or the predicted Met-Hb could be added to the "Total-Hb minus Met-Hb" described above, for a determination of Total-Hb. Method 2 defined above, is an accurate method of obtaining Total-Hb in the presence of Met-Hb.

A primary calibration algorithm for "Total-Hb minus Met-Hb" may be developed using samples in the primary calibration set that contain various amounts of Oxy-Hb, Deoxy-Hb, Carboxy-Hb, and Met-Hb. It is preferred if the amounts of Oxy-Hb, Deoxy-Hb, and Carboxy-Hb, are summed to produce the concentration of Total-Hb (which is actually "Total-Hb minus Met-Hb") in the reference values. The name of the substance used as an indicator of hemolysis is usually the same as the substance or substances included in the reference values. However, it should be understood that the actual substance or substances included in the reference values depend on the composition of the primary calibrators. It should also be understood that some primary calibration samples should have zero amounts of one or more than one of the constituents, and that a sample with zero amount of the constituent could still be considered as a sample with the constituent, wherein the concentration of the constituent is zero g/L (or whatever unit is used to quantify the amount).

It should be understood that Method 1 can be used if the accuracy of the estimated Total-Hb obtained using Method 1, is acceptable for the particular application.

In an aspect of the present invention, the terms of the primary calibration algorithm for "Total-Hb minus Met-Hb," and the terms of the primary calibration algorithm for Met-Hb are added to produce a set of terms for a single calibration algorithm, which predicts a corrected Total-Hb.

In yet another aspect of the present invention, the indicator of hemolysis is Oxy-Hb, and a corrected Total-Hb value can be obtained by adding the predicted values for Oxy-Hb and Met-Hb. To those skilled in the art, it will be understood that a significant proportion of Deoxy-Hb and/or Carboxy-Hb, if present in a sample, could be measured as Oxy-Hb.

As noted above, about 95% of the Hb in a hemolyzed sample or whole blood sample is usually in the Oxy-Hb state, unless the blood donor was recently exposed to carbon monoxide or the person suffers from methemoglobinemia. Exposure to carbon monoxide (mainly due to smoke inhalation) causes an elevation of Carboxy-Hb, and methemoglobinemia causes an elevation of Met-Hb. Oxidation of the iron in the heme moiety of Hb molecules, is a normal process that occurs in vivo. Enzymes are continually at work reversing the process and thus preventing the accumulation of Met-Hb (for example, NADH methemoglobin reductase, and the met-Hb reductase system). Methemoglobinemia is a condition of people that lack enzymes required to reverse this oxidation process. Absence of the enzymes that reverse the oxidation process, also results in spontaneous oxidation of Hb to Met-Hb in hemolyzed serum or plasma over time, causing the sample to darken in the color.

FIG. 3 shows how the absorbance spectra of a hemolyzed sample changes as it ages. The absorbance peak at about 632 nm that accompanies the darkening of color indicates a conversion of Hb to Met-Hb. Accumulation of Met-Hb could also occur in serum or plasma of patients infused with Hb-based blood substitutes. A calibration algorithm for Met-Hb in hemolyzed serum or plasma samples or in a serum or plasma sample from a patient infused with Hb-based blood substitutes can therefore be developed, preferably using the negative absorbance slope of the peak with an absorbance maximum at about 630 nm. Example 6 (Equation 22) gives an example of a primary calibration algorithm for Met-Hb, which uses 645 nm as the principal calibration wavelength.

The measurement of Met-Hb as described herein, is used in the measurement of an indicator of hemolysis in serum, plasma, urine, cerebrospinal fluid, lymphatic fluid and synovial fluid, for measuring the oxidation of Hb into Met-Hb, and also for measuring the oxidation of Hb-based blood substitutes into their Met-Hb form. Also, the measurement of Met-Hb as described herein, is used in the measurement of Hb in whole blood of patients who are or who are not infused with Hb-based blood substitutes.

In another aspect of the present invention there is provides a method of measuring a corrected Total-Hb using the following primary calibration algorithms:
1. A primary calibration algorithm for predicting Oxy-Hb or "Oxy-Hb plus Deoxy-Hb;"
2. A primary calibration algorithm for predicting Met-Hb; and
3. A primary calibration algorithm for predicting Carboxy-Hb.

Total Hb can then be measured by adding the predicted values for each of "Oxy-Hb plus Deoxy-Hb", Met-Hb, and Carboxy-Hb that are determined using the primary calibration algorithms defined above.

Alternatively, the terms of the primary calibration algorithms identified above for "Oxy-Hb plus Deoxy-Hb", Met-Hb, and Carboxy-Hb may be added to produce a single set of terms for a single calibration algorithm, which predicts the Total-Hemoglobin. The use of a single calibration algorithm that predicts Total-Hb may be used to determine Corrected Total-Hb. If the sample used is an aerobic sample, then there is no need to develop separate calibration algorithms for Oxy-Hb and Deoxy-Hb. For example, if the sample is venous blood (which has a higher proportion of Deoxy-Hb compared to a capillary or an arterial blood sample), the atmospheric oxygen will rapidly convert most of the Deoxy-Hb to Oxy-Hb. Preferably the sample is whole blood, but the use of any other sample, for example serum and plasma, is considered to be within the scope of the present invention. When the sample is whole blood, the sample is preferably obtained by a pin prick. Lysis of the red blood cells (RBCs) is not required because the calibration algorithm, or calibration algorithms, are capable of functioning with or without the presence of highly light-scattering particles like chylomicrons and more importantly, RBC's.

Yet another aspect of one of the methods of the present invention is to provide yet another method of measuring a corrected Total-Hb using the following primary calibration algorithms:
1. A primary calibration algorithm for predicting Oxy-Hb or "Oxy-Hb plus Deoxy-Hb";
2. A primary calibration algorithm for predicting Met-Hb;
3. A primary calibration algorithm for predicting Carboxy-Hb; and
4. A primary calibration algorithm for predicting Sulf-Hb.

Total Hb can be measured by adding the predicted values for each of "Oxy-Hb plus Deoxy-Hb," Met-Hb, Carboxy-Hb, and Sulf-Hb using the primary calibration algorithms as just defined. Alternatively, the terms of the first, second, third, and fourth primary calibration algorithms for "Oxy-Hb plus Deoxy-Hb", Met-Hb, Carboxy-Hb, and sulf-Hb can be added to produce a single set of terms for a single calibration algorithm, which predicts Total-Hemoglobin (Total-Hb). The use of a single calibration algorithm that predicts Total-Hb may be used to determine Corrected Total-Hb. If the sample used is an aerobic sample, then as indicated above, there is no need to develop separate calibration algorithms for Oxy-Hb and Deoxy-Hb atmospheric oxygen will rapidly convert most of the Deoxy-Hb to Oxy-Hb. Preferably the sample is whole blood, but the use of any other sample, for example serum and plasma, is considered to be within the scope of the present invention. When the sample is whole blood, the sample is preferably obtained by a pin prick, and lysis of the RBC's is not required because the calibration algorithms is capable of functioning with or without the presence of highly light-scattering particles like chylomicrons and more importantly, RBC's.

Oxidation of Hemoglobin

Oxidation of the iron in the heme moiety of Hb molecules is a normal process that occurs in vivo. Enzymes are continually at work reversing the oxidation process and thus preventing the accumulation of Met-Hb. Methemoglobinemia is a condition of people that lack enzymes, e.g., NADH methemoglobin reductase, required to reverse the oxidation process. The Met-Hb reductase system may be underdeveloped in infants, making methemoglobinemia more prevalent among infants. Another reason for the higher incidence of methemoglobinemia among infants and neonates is an underdeveloped gastrointestinal system in some infants. In an underdeveloped gastrointestinal system, bacteria level could rise due to a decrease secretion of gastric acid. Nitrates are usually converted into nitrites by bacteria of the gastrointestinal system, and the nitrites in turn react with the Hb to produce Met-Hb.

Lack of Met-Hb reductase enzymes in hemolyzed serum causes spontaneous oxidation of Hb to Met-Hb over time, causing the sample to darken in the color. With reference to FIG. 3, the absorbance peak at about 632 nm that accompanies the darkening of color and that indicates a conversion of Hb to Met-Hb can be observed. Accumulation of Met-Hb could also occur in patients who are not lacking the Met-Hb reductase enzymes. In these patients, the accumulation of Met-Hb could be induced by the intake of certain therapeutic drugs and other chemicals, for examples, which should not be considered limiting in any way: dapsone, chloroquine, phenazopyridine, phenacetin, nitrates, nitrites, phenols, and aniline. Patients with high levels of Met-Hb, whatever the cause, should be monitored for the increase of Met-Hb, or the decrease of Met-Hb after treatment, or both the increase and decrease.

In a normal person, the composition of Hb (% of Tot-Hb) in the arterial blood is about 95% Oxy-Hb, about 2% Deoxy-Hb, about 2% Carboxy-Hb and about 1% Met-Hb, as measured by CO-oximetry. In a heavy smoker, the % Carboxy-Hb can be about 10%. It should be understood that the Hb composition depends on the CO-oximeters used to measure the % of the Hb species. Newer CO-oximeters tend to give different numbers, which are supposedly more reliable, since the measurements in the newer CO-oximeters are performed at more wavelengths. More wavelengths could help compensate for interfering substances like, for example, bilirubin, turbidity, Sulfhemoglobin, and fetal hemoglobin. It should also be understood that although CO-oximeters are considered by some as reference instruments for measuring the % Hb species, the methods using CO-oximeters are not true reference methods for measuring the % of the Hb species in a blood sample.

The Total-Hb and Met-Hb could be measured in a pinprick blood sample and the % Met-Hb calculated. The calibration algorithm for measurement of % Met-Hb could also be developed empirically by taking the ratio of absorbances of a sample at two different wavelengths, for example about 630 nm and about 560 nm. With reference to FIG. 2, it can be noted that the absorbance at about 630 nm is greater for Met-Hb than for the same amount of each of the other species shown; the reverse is true at about 560 nm. These wavelengths are just examples that can be used, and should not be considered limiting in any way.

Furthermore, the ratio of absorbances at 560 nm and 940 nm, could be one of more than one ratio term in a calibration algorithm for % Met-Hb. It should be understood, that the use of ratio of absorbances as a single term, or the use of the sum of more than one similar term in a calibration algorithm is preferred. However, any statistical technique used to develop a calibration algorithm is considered to be within the scope of the present invention. A method for correcting the measurement of Tot-Hb (used as an indicator of hemolysis in serum and plasma), for the presence of Met-Hb is disclosed in U.S. Pat. No. 6,689,612 (Samsoondar; which are incorporated herein by reference). The methods described for calibration of Met-Hb, correcting Total-Hb for the presence of Met-Hb, and flagging Total-Hb for the presence of Met-Hb, could also be used for whole blood samples.

Degradation and Reversal of Degradation of Hemoglobin-Based Blood Substitutes

Blood transfusion is a life-saving process that is performed after severe blood loss after trauma or during surgery. Some advantages of using a blood substitute instead of whole blood (by "whole blood" it is meant the combination the cellular and non-cellular components of blood) or red blood cells are as follows:
  a) blood substitutes are expected to be universally compatible with all blood types, therefore cross matching would not be necessary;
  b) maximum storage time of blood is 42 days, whereas the blood substitutes could have a much longer shelf life; and
  c) the purification process of the blood substitute may include heat treatment, which can minimize the threat of hazardous viruses.

Most blood substitutes under development are made from human Hb, bovine Hb, or recombinant DNA technology (recombinant Hb). Hemoglobin comprises four protein subunits, which are two pairs of identical polypeptide chains. Each subunit has a molecular weight of about 16,000, with a cleft that contains a heme (iron-porphyrin) group, the site of oxygen uptake. The subunits are not covalently linked, and require the red cell membrane to keep the subunits together. A hemoglobin molecule is too large to penetrate the kidney, but the subunits are small enough to become lodged in the kidney and cause kidney failure.

In Hb-based blood substitutes, the subunits of the Hb could be chemically cross-linked with each other or to large polymers, or the Hb molecules could be linked to other Hb molecules to form poly-Hb, for stability. The Hb subunits may be inter- or intra-molecularly cross-linked. Regardless of the protein or polymer surrounding the heme groups, the absorbance spectrum of Hb-based blood substitutes is almost identical to normal Hb, but subtle differences at certain wavelengths may be present. The Hb-based blood substitutes are not protected from uncontrollable spontaneous oxidation into Met-Hb since they are no longer housed within the red cell membrane, where the Hb is usually in contact with Met-Hb reductase enzymes. A detailed review of blood substitutes is provided in volumes I and II of "Blood Substitutes: Principles, Methods, Products and Clinical Trials" (1998, by T. M. S. Chang, published by Karger Landes Systems). It should be understood that any form of Hb-based blood substitutes is considered to be within the scope of the present invention.

Due to the absence of the Met-Hb reductase enzymes, accumulation of Met-Hb could occur in the plasma of patients infused with Hb-based blood substitutes. Measurement or calculation of the ratio of Met-Hb to Total-Hb is useful for monitoring the degradation of Hb-based blood substitutes to its Met-Hb form, or for monitoring the reversal of degradation (e.g. degradation due to oxidation) process after for example, administration of one or more therapeutic agents, or monitoring a retardation in the spontaneous oxidation process by encapsulating the Hb-based blood substitutes with enzymes like NADH methemoglobin reductase or other reducing agents. In this example, the two blood analytes are the Hb-based blood substitute, and the Met-Hb form of the Hb-based blood substitute. In a patient infused with one or more types of Hb-based blood substitutes, it should be understood that the Total-Hb could include both the one or more Hb-based blood substitutes and endogenous Hb, and the Met-Hb could include both the Met-Hb forms of the one or more Hb-based blood substitutes and endogenous Met-Hb.

A method for monitoring degradation (e.g., oxidation) of Hb-based blood substitutes requires development of calibration algorithms for Met-Hb and the Hb-based blood substitute. The calibration algorithms can be developed by optionally using any statistical technique to process EMR absorbed by a sample at one or more wavelengths. The concentration of the one or more Hb-based blood substitutes and the Met-Hb can then be determined by applying the respective calibration algorithm to the absorbance of the sample at one or more wavelengths. Using a calibration algorithm for Met-Hb and another calibration algorithm for the Hb-based blood substitute, will allow the Met-Hb to be reported as a proportion, fraction, or percent of the total Hb-based blood substitute. Alternatively, a calibration algorithm could be developed for the proportion, fraction, or percent of the total Hb-based blood substitute, which is in the form of Met-Hb.

A single blood sample or more than one blood sample collected over time may be used to determine the degradation status of Hb-based blood substitutes, to determine the reversal of degradation of Hb-based blood substitutes. More than one blood sample collected over time is preferred. The concentration of Met-Hb as well as the % Met-Hb may be used to monitor degradation and reversal of degradation of Hb-based blood substitutes. As an example, which is not to be considered limiting, when a single sample is used, an amount of at least about 3% Met-Hb, is an indication of degradation of blood substitutes. Therefore, samples characterized as having 3% or more of Met-Hb may be identified as exhibiting degradation of a Hb-based blood substitute. Preferably, more than one blood samples are collected over time, and an increase in concentration of Met-Hb, or an increase in % Met-Hb, is an indication of degradation of blood substitutes. Furthermore, a decrease in concentration of Met-Hb or a decrease in % Met-Hb over time is an indication of reversal of degradation of blood substitutes Therefore, the present invention provides a method of monitoring degradation or reversal of degradation of one or more Hb-based blood substitutes in a sample comprising:
  i) determining a first concentration of Met-Hb, and a first concentration of the one or more than one Hb-based blood substitutes in the sample, by applying a first calibration algorithm for the Met-Hb, and a second calibration algorithm for the one or more than one Hb-based blood substitutes, to an order derivative of absorbance of the sample at one or more wavelength of a standard set of wavelengths;

ii) determining a second concentration of the Met-Hb and a second concentration of the one or more than one Hb-based blood substitutes in the sample at a second time, by applying a first calibration algorithm for the Met-Hb, and a second calibration algorithm for the one or more than one Hb-based blood substitutes, to an order derivative of absorbance of the sample at one or more wavelength of a standard set of wavelengths; and iii) calculating a first proportion of the one or more than one Hb-based blood substitutes that is in the form of Met-Hb using the first concentration of Met-Hb and the first concentration of the one or more than one Hb-based blood substitutes, and calculating a second proportion of the one or more than one Hb-based blood substitutes that is in the form of Met-Hb using the second concentration of Met-Hb and the second concentration of the one or more than one Hb-based blood substitutes;

where an increase in the second proportion, when compared to the first proportion is an indication of degradation of the one or more than one blood substitute, and a decrease in the second proportion, when compared to the first proportion is an indication of a reversal of degradation of the one or more than one Hb-based blood substitute, thereby monitoring degradation or reversal of degradation of the one or more Hb-based blood substitutes.

Also the present invention includes a method of determining degradation of one or more than one Hb-based blood substitute in a sample, comprising:

i) measuring an absorbance of the sample at one or more than one wavelengths of a standard set of wavelengths using a spectroscopic apparatus comprising, a calibration algorithm for Met-Hb and one or more than one calibration algorithm for the one or more than one Hb-based blood substitute;

ii) calculating a first concentration of the Met-Hb from the absorbance, by applying the calibration algorithm for Met-Hb to an order derivative of the absorbance, and calculating a second concentration of the one or more Hb-based blood substitute from the absorbance, by applying the one or more than one calibration algorithm for the Hb-based blood substitutes to an order derivative of the absorbance;

where, if the first concentration of the Met-Hb is greater than or equal to 3% of the second concentration of the one or more than one Hb-Based blood substitute, then this indicates degradation of the one or more than one Hb-based blood substitute.

U.S. patent application Ser. No. 10/136,329, now U.S. Pat. No. 6,949,384 (Publication Number 2003-0138960 A1; Samsoondar; which are incorporated herein by reference), describes a method of monitoring the degradation of Hb-based blood substitutes by monitoring the production of the Met-Hb derivative of the Hb-based blood substitutes. The application teaches that the sample can be whole blood, serum, plasma, or a body part from the patient infused with the blood substitute. The same method can also be used to monitor degradation of stock Hb-based blood substitutes. By a "Stock Hb-based blood substitute," it is meant a manufactured Hb-based blood substitute that is ready for use, for example, which should not be considered limiting in any way, for infusion by a patient. A method for correcting the measurement of Tot Hb (used as an indicator of hemolysis in serum and plasma), for the presence of Met-Hb is disclosed in U.S. Pat. No. 6,689,612 (Samsoondar; which are incorporated herein by reference).

The above description is not intended to limit the claimed invention in any manner. The present invention will be further illustrated in the following examples.

EXAMPLES

Primary Calibration

Primary calibration of an apparatus is a cumbersome, time intensive exercise because it requires the measurements of absorbance of a relatively large set of samples, referred to as primary calibration sets. The samples in the primary calibration set should be real or very close to real samples. Preferably, samples include all the absorbance variability expected in a sample, whereby the sample variability becomes built into the primary calibration algorithm. Vessels also contribute variability, and it is possible to develop one or more primary calibration algorithm using a combination of more than one vessel, whereby the vessel variability becomes built into the primary calibration algorithm. However, development of primary calibration algorithms that are specific to a particular type of vessel is preferred. The apparatus on which primary calibration is performed is referred to as the "First Apparatus". Another apparatus that uses a primary calibration algorithm or a modified form of the primary calibration algorithm, without the second apparatus itself undergoing the process of primary calibration, is referred to as a "Second Apparatus".

A primary calibration algorithm can be obtained as follows: Absorbance spectra are obtained for several samples that cover a concentration range of a given analyte for which the primary calibration algorithm is being developed. It is preferred that the samples include all the absorbance variability expected in a sample, whereby the sample variability becomes built into the primary calibration algorithm. A multiple linear regression is then performed to develop a linear combination having the order derivative of absorbance at specific wavelengths as the independent variable, and the concentration of the analyte as the dependent variable. Other statistical methods, for example simple linear regression that uses only one wavelength, partial least squares (PLS) and principal component analysis (PCA), may also be used. The equation thus obtained is a primary calibration algorithm.

Zero order derivative of absorbance (also referred to as raw absorbance) or any order derivative of absorbance may be used in the calibration process with second order derivative of absorbance being preferred, and first order derivative of absorbance being more preferred. One exception is for a simulator of turbidity (for example IL), where both zero order derivative of absorbance and the first derivative of absorbance are preferred. With respect to a lipid emulsion, for example IL, for samples in containers that attenuate light in a reproducible manner, zero order derivative of absorbance is preferred over first order derivative of absorbance, because the resulting primary calibration algorithm covers a wider analytical range i.e. a wider range wherein the relationship between the predicted values and actual concentrations of a lipid emulsion, for example IL, is linear. For samples in, for example, blood bag tubing, which may or may not contain black writing in the light path, as discussed in U.S. Pat. No. 6,268,910 B1, the first order derivative of absorbance is preferred.

Software tools used for developing primary calibration algorithms may comprise but are not limited to the following:

Matlab™ used to create programs for smoothing absorbances and obtaining derivative of absorbances.

MS Excel™ may be used to develop macros for calculating derivative of absorbances; StatView™ used to create algorithms by a process called "step-wise multiple linear regression." In the step-wise linear regression, the order derivative of absorbance measurements for all the wavelengths is presented to the StatView™ program; only the wavelengths at which the order derivative of absorbance contribute to the calibration fit at a predetermined level of significance are selected for the algorithms.

Pirouette™ may be used to create calibration algorithms by PLS or PCA, using the measurements for all the wavelengths, or selected sections of the absorbance spectra.

It will be appreciated however that other software tools may also be used. It will also be appreciated that any statistical technique may be used for the preparation of a calibration algorithm, for example, which should not be considered limiting in any way, simple linear regression, multiple linear regression, and multivariate data analysis.

Examples of multivariate data analysis, which should not be considered limiting in any way, are Principal Component Analysis (PCA), Principal Component Regression (PCR), Partial Least Squares regression (PLS), Neural Networks and Genetic Algorithms Software tools used for developing primary calibration algorithms may comprise, but are not limited to the following:

Matlab™ used to create programs for smoothing absorbances and obtaining order derivative of absorbances.

MS Excel™ may be used to develop macros for calculating order derivative of absorbances;

StatView™ used to create algorithms by a process called "step-wise multiple linear regression." In the step-wise linear regression, the order derivative of absorbance measurements for all the wavelengths is presented to the StatView™ program; only the wavelengths at which the order derivative of absorbance contribute to the calibration fit at a predetermined level of significance are selected for the algorithms.

Pirouette™ may be used to create calibration algorithms by PLS or PCA, using the measurements for all the wavelengths, or selected sections of the absorbance spectra.

Calibration algorithms may also include the techniques of Neural Network and Genetic Algorithms, although any statistical technique is considered to be within the scope of the present invention.

It will be appreciated however that other software tools may also be used. Many examples of the primary calibration procedure, in respect of blood analytes, are shown in the references incorporated within this application. It will be appreciated that a primary calibration algorithm may contain from a single wavelength term, in the simplest case, to multiple terms that use many wavelengths. Primary Calibration Algorithms can be obtained by a process of simple linear regression, multiple linear regression, multivariate analysis or a combination thereof. Some examples of multivariate analysis are PLS, PCA, Genetic Algorithm, and Neural Network.

It should be understood that any order derivative of absorbance can be used, and it should also be understood, that the robustness of a primary calibration algorithm depends on the inclusion of interfering substances in the primary calibration sets, one expect to encounter in real samples. The chemometrics methods referred to should not be considered limiting in any way, and any form of chemometrics and data processing are within the scope of the present invention.

It will also be appreciated that determination of analyte concentration in a sample in a second apparatus may be accomplished by using data pre-processing, including smoothing, calculation of first and higher order derivative of absorbance, interpolation of absorbances, multiplicative scatter correction, or data transformation. Similar data pre-processing may also be used prior to primary calibration algorithm development. Photometric correction may also be used on second apparatus depending on the required accuracy of the predicted value of an analyte concentration.

Any other methods of primary calibration algorithm development and any form of data transformation are within the scope of this invention. Example of data transformation, which should not be considered limiting in any way, include determining the log and anti-log of the analyte concentration, and Fourier transformation, which are well known to those skilled in the art (for example see Osborne, B. G., Fearn, T & Hindle, P. H., Practical NIR Spectroscopy with Applications in Food and Beverage Analysis, 1993, Published by Longman Scientific & Technical, which is incorporated herein by reference).

The primary calibration algorithms can vary in robustness, depending on the make up of the primary calibrators. Once a primary calibration algorithm has been obtained for a given analyte, the concentration of the analyte in a sample (i.e. a predicted value) can be determined by obtaining an absorption spectrum of the sample and applying the primary calibration algorithm for the analyte. Primary calibration algorithms for any number of analytes can be installed in an apparatus, and they can be applied to the same absorbance data, in order to obtain concentrations of the analytes. Furthermore, more than one primary calibration algorithm can be installed for one analyte. The use of multiple primary calibration algorithms may be used to extend the analytical range of the spectroscopic apparatus at higher or lower analyte concentrations.

It should be understood that the analytes disclosed herein are by way of example only, and they should not limit the use of the apparatus of the present invention in any way.

Development of Primary Calibration Algorithms

The examples given below mostly describe analytes in plasma. However, it should be understood that similar methods of calibration algorithm development for analytes in other types of samples, for example, which should not be considered limiting in any way, calibrators, whole blood, serum, plasma, urine, synovial fluid, lymphatic fluid, sputum, feces, dairy products, beverages, a body part, for example but not limited to, a finger, arm, ear lobe, or a pharmaceutical tablet which should not be considered limiting in any way, are within the scope of the present invention.

Primary calibration algorithms may be developed by trial-and-error, without using an extinction coefficient at each relevant wavelength, for an analyte to be measured.

CO-oximetry is a method where more than one calibration algorithm is used to predict more than one analyte (for example, Oxy-Hb, Deoxy-Hb, Carboxy-Hb, and Met-Hb), and where the extinction coefficients for each of Oxy-Hb, Deoxy-Hb, Carboxy-Hb, Met-Hb are used in the calibration algorithms. CO-oximeters are recalibrated with a Total-Hb (the sum of Oxy-Hb, Deoxy-Hb, Carboxy-Hb, and Met-Hb) calibrator, and during the recalibration process, the coefficients of the calibration algorithms are modified. Some CO-oximeters may provide a measurement of Sulf-Hb, for example AVL OMNI available from Roche Diagnostics.

However, the use of extinction coefficients is not preferred in the present invention because of the light-scattering effect of RBC's.

In an aspect of the present invention, Deoxy-Hb may be converted into Oxy-Hb by exposing the sample to atmospheric oxygen, thereby eliminating the need to differentiate Oxy-Hb from Deoxy-Hb. A sample of known "Oxy-Hb plus Deoxy-Hb" concentration, where the "Oxy-Hb plus Deoxy-Hb" fraction is about 95% of the Total-Hb, can be considered to have a Total-Hb concentration of same value as the "Oxy-Hb plus Deoxy-Hb" concentration. Similarly, a sample of known Total-Hb concentration that comprises about 95% "Oxy-Hb plus Deoxy-Hb," can be considered to have an "Oxy-Hb plus Deoxy-Hb" concentration of the same value as the Total-Hb concentration.

The term "Oxy-Hb" and "Oxy-Hb plus Deoxy-Hb" can be used interchangeable when the sample is exposed to atmospheric oxygen since the Deoxy-Hb quickly absorbs oxygen and becomes converted to Oxy-Hb. Therefore, the reference value, whether labelled as Oxy-Hb or "Oxy-Hb plus Deoxy-Hb", can be a measurement of either Oxy-Hb or "Oxy-Hb plus Deoxy-Hb."

To prepare a primary calibration algorithm for hemoglobin, sixty serum specimens with no visible interferents were stored refrigerated or frozen until used. More or fewer specimens may be used so long as a sufficient number is used to provide robust algorithm(s). Hemoglobin (Hb), INTRALIPID (IL), bilirubin (BR) and biliverdin (BV) were added to the normal sera to give final concentrations of 0-6.1 g/L, 0-5.1 g/l, 0-42.7 mg/dL, and 0-4.4 mg/dL respectively. Stock Hb was prepared by replacing the plasma (free from all interferents) from a blood sample, with twice its volume of water, and lysing the cells through three freeze-thaw cycles. For each cycle the blood was left in the freezer for 45-60 minutes, and then removed and placed on a rocker at room temperature for 30-45 minutes.

Hb content of the lysate was measured by a spectroscopic method for measuring oxy-Hb described by Tietz ((Tietz Textbook of Clinical Chemistry, $3^{rd}$ Ed, 1999, pp 1674-1676), after removing the RBC debris and unlysed RBC's by centrifuging at 10,000×g for 10 minutes. Any method that provides a reliable determination of Hb content may be used. A typical hemolysate contains approximately 100 g/L Hb. CO-oximetry suggests that more than 95% of the Hb is in the oxy-Hb state. Stock BV was prepared by dissolving biliverdin dihydrochloride (obtained from Sigma) initially in 50% methanol-50% water, and diluting further with phosphate buffered saline (PBS). Stock IL also known as TRAVAMULSION™ (preferably obtained from Clintec-Nestle & Baxter) has a concentration of 10%. Stock BR was prepared by dissolving Ditauro-Bilirubin (from Porphyrin Products, Logan, Utah, USA) in interferent-free serum, to a concentration of 500 mg/dL. The spectral absorbance data were recorded for the 60 samples using different polypropylene dispensing tips. Out of the 60 samples, odd numbers were used for the calibration set, and even numbers were used as the validation set. This primary calibration set does not contain Met-Hb or MB, therefore these substances may contribute to inaccuracies in the Hb measurements. Met-Hb and MB may be included in the absorbance variability of the primary calibration set, in order to obtain more robust primary calibration algorithms.

A summary of exemplary primary calibration algorithms, which are not to be considered limiting in any manner, using the methods as described herein are presented in Table 1. It is to be understood that other primary calibration algorithms may be readily obtained using different substances, or sample containers, etc, and using the methods as described herein

TABLE 1

Wavelengths used in primary calibration algorithms shown in Examples 1 to 7, arranged according to analyte.

| Equation No. | Analyte | Wavelengths (nm) | | | |
|---|---|---|---|---|---|
| | | 1 | 2 | 3 | 4 |
| 1 | Hb | 584 | 599 | 617 | — |
| 2 | Hb | 600 | 618 | — | — |
| 3 | Hb | 591 | 653 | — | — |
| 4 | Hb | 600 | 663 | — | — |
| 5 | Hb | 558 | 570 | 730 | — |
| 6 | Hb | 591 | 610 | — | — |
| 7 | Hb-based Blood Substitute | 541 | 558 | 600 | 616 |
| 8 | BV | 649 | 731 | 907 | — |
| 9 | BV | 724 | 803 | — | — |
| 10 | BV | 718 | 781 | — | — |
| 11 | BR | 524 | 587 | 602 | — |
| 12 | BR | 534 | 586 | — | — |
| 13 | BR | 504 | 518 | 577 | — |
| 14 | BR | 495 | 512 | 578 | — |
| 15 | BR | 511 | 554 | — | — |
| 16 | IL | 700 | — | — | — |
| 17 | IL | 872 | — | — | — |
| 18 | IL | 988 | 1038 | — | — |
| 19 | IL | 874 | — | — | — |
| 20 | IL | 874 | — | — | — |
| 21 | IL | 900 | — | — | — |
| 22 | Met-Hb | 645 | 669 | — | — |
| 23 | MB | 702 | 759 | — | — |
| 24 | MB | 677 | 953 | — | — |

Also, the lowest and highest wavelengths shown in Table 1 are 504 nm and 1038 nm respectively, but it should be understood that calibration wavelengths within the range of about 300 nm to about 2500 nm, or any wavelength range therebetween, are within the scope of this invention.

Example 1

Calibration Algorithms for Hb

Examples of primary calibration algorithms for Hb using the method described in the present application are given below. It will be appreciated that the algorithms can differ when the conditions in which they are obtained differ. Although the examples below show "g/L Hb" as the dependant variable, it should be understood that the dependant variable could be any indicator of hemolysis related to Hb, for example, Total-Hb, Oxy-Hb and "Total-Hb minus Met-Hb." The true indicator of hemolysis depends on both the reference method used to measure the indicator of hemolysis, and the substances included in the primary calibration set. As another aspect of this invention, methods for making corrections to the indicator of hemolysis are described, and whether correction is performed on the indicator of hemolysis, or the value of the indicator of hemolysis is only flagged to indicator potential error in the value, depends on the required accuracy of the indicator of hemolysis. It should be understood that measurement of Hb in whole blood is considered to be within the scope of the present invention.

Equation 1 (obtained using disposable polypropylene dispensing tips)

$$\text{g/L Hb}=-16.81(1\text{st D A}584)+79.47(1\text{st D A}599)-60.95(1\text{st D A}617)+0.24$$

where (1st D A) is the first derivative of the absorbance measurement at the wavelength specified in nanometers.

Equation 2 (Obtained using 12 mm disposable polypropylene tubes $$\text{g/L Hb} = 113.27(1\text{st D A}600) - 182.94(1\text{st D A}618) - 0.13$$

where (1st D A) is the first derivative of the absorbance measurement at the wavelength specified in nanometers.

The following other examples of primary calibration algorithms for Hb are described in U.S. Pat. Nos. 6,268,910 B1 and 5,846,492, WO 98/39634 and WO 97/47972.

Equation 3 (obtained using blood tubing)

$$\text{g/L Hb} = 45.68(1\text{st D A}591) - 47.48(1\text{st D A}653) - 0.42$$

where (1st D A) is the first derivative of the absorbance measurement at the wavelength specified in nanometers.

Equation 4 (obtained using disposable plastic dispensing tips)

$$\text{g/L Hb} = 15.89(1\text{st D A}600) - 15.88(1\text{st D A}663) - 0.21$$

where (1st D A) is the first derivative of the absorbance measurement at the wavelength specified in nanometers.

Equation 5 (obtained using disposable plastic dispensing tips)

$$\text{g/L Hb} = 30.72(1\text{st D A}558) - 17.40(1\text{st D A}570) + 171.14(1\text{st D A}730) - 072$$

where (1st D A) is the first derivative of the absorbance measurement at the wavelength specified in nanometers.

Equation 6 (obtained using translucent pipette tips)

$$\text{(g/L) Hb} = 30.14(1\text{st D A}591) - 27.98 \,(610)$$

where (1st D A) is the first derivative of the absorbance measurement at the wavelength specified in nanometers.

Example 2

Calibration Algorithms for Hb-based Blood Substitutes

The following is an example of a primary calibration algorithm for Hb-based blood substitute as described in WO 98/39634.

Equation 7 (Obtained using disposable polypropylene dispensing tips)

$$\text{g/L Hb-based blood substitute} = 23.97(1\text{st D A}541) - 76.01(1\text{st D A}558) + 130.84(1\text{st D A}600) - 113.61(1\text{st D A}616) + 0.30$$

where (1st D A) is the first derivative of the absorbance measurement at the wavelength specified in nanometers.

Example 3

Calibration Algorithms for Biliverdin

The following examples of primary calibrations algorithms for biliverdin are described in U.S. Pat. Nos. 6,268,910 B1 and 5,846,492 and WO 97/47972.

Equation 8 (obtained using blood bag tubing)

$$\text{mg/L BV} = -45.40(1\text{st D A}649) + 323.15(1\text{st D A}731) - 493.79(1\text{st D A}907) - 1.14$$

where (1st D A) is the first derivative of the absorbance measurement at the wavelength specified in nanometers.

Equation 9 (obtained using disposable plastic dispensing tips)

$$\text{mg/L BV} = 98.07(1\text{st D A}724 \text{ nm}) - 122.73(1\text{st D A}803 \text{ nm}) + 0.07$$

where (1st D A) is the first derivative of the absorbance measurement at the wavelength specified in nanometers.

Equation 10 (obtained using translucent pipette tips)

$$\text{mg/dL BV} = 160.29(1^{st}\text{D A}718) - 206.15\,(1^{st}\text{D A}781) + 1.42$$

where (1st D A) is the first derivative of the absorbance measurement at the wavelength specified in nanometers.

Example 4

Calibration Algorithms for Bilirubin

The sample set used for Hb calibration is not typically used for BR calibration, because the absorbance due to either Hb>4 g/L or IL>4 g/L, approaches the limit of the apparatus in the region around 524 nm, a primary wavelength used for BR calibration. Instead, a separate set of 60 samples were prepared and tested. As will be readily appreciated by those skilled in the art, the sample set used for primary calibration should be of a size sufficient to include most of the variability encountered with actual patient samples, such as serum or plasma. The samples were prepared as before by adding Hb, IL, BR and BV to the normal sera to give final concentrations of 0-2.6 g/L, 0-3.6 g/l, 0-37 mg/dL, and 0-4.4 mg/dL respectively. The spectral absorbance data were recorded for the 60 samples using different polypropylene dispensing tips. Out of the 60 samples, odd numbers were used for the calibration set, and even numbers were used as the validation set. The stock interferents were prepared as described above for Hb, and the BR concentrations were adjusted by the factor 1.23. The 1.23 factor that was derived previously from the slope of the regression line obtained from a validation set using real icteric serum and plasma samples. Met-Hb and MB is not expected to interfere with BR predictions, but they can only help to create more robust primary calibration algorithms, if they were included in the absorbance variability of the primary calibration set.

Equation 11 (obtained using disposable polypropylene dispensing tips)

$$\text{mg/dL BR} = 293.1(1\text{st D A}524) + 327.8(1\text{st D A}587) - 451.7(1\text{st D A}602) - 7.5$$

where (1 st D A) is the first derivative of the absorbance measurement at the wavelength specified in nanometers.

Equation 12 (obtained using 12 mm disposable polypropylene tubes)

$$\text{mg/dL BR} = 406.04(1\text{st D A}534) + 183.94(1\text{st D A}586) - 2.27$$

where (1st D A) is the first derivative of the absorbance measurement at the wavelength specified in nanometers.

The following examples of primary calibrations algorithms for bilirubin are described in U.S. Pat. No. 6,268,910 B1, U.S. Pat. No. 5,846,492 and WO 97/47972.

Equation 13 (obtained using blood bag tubing)

$$\text{mg/dL BR} = -43.03(1\text{st D A}504) + 252.11(1\text{st D A}518) + 240.03(1\text{st D A}577) - 2.89$$

where (1st D A) is the first derivative of the absorbance measurement at the wavelength specified in nanometers.

Equation 14 (Obtained using disposable plastic dispensing tips)

mg/dL BR=−24.88(1st D A495)+201.61(1st D A512)+44.98(1st D A578 nm)−6.48 where (1st D A) is the first derivative of the absorbance measurement at the wavelength specified in nanometers.

Equation 15 (obtained using translucent pipette tips)

mg/dL BR=142.09(1$^{st}$ D A511)+89.9(1$^{st}$ D A554)−4.47 where (1st D A) is the first derivative of the absorbance measurement at the wavelength specified in nanometers.

Example 5

Calibration Algorithm for Turbidity

Turbidity in serum and plasma is caused mainly by the presence of fat particles, particularly chylomicrons. INTRALIPID™ (IL) is a lipid emulsion that simulates naturally-occurring chylomicrons, and therefore may preferably be used to simulate turbidity in serum and plasma.

Samples used for Hb and BR calibration are preferably not used for IL calibration because the Hb stock solution contributes significant light scattering (like lipid particles) due to unlysed RBC's and RBC fragments. Centrifugation of the hemolysate was unable to remove all the unlysed RBC's and RBC fragments.

Forty samples of PBS (phosphate buffered saline) were spiked with 10% Intralipid™ to produce concentrations of 0-20 g/L. The spectral absorbance data were recorded for the 40 samples using different polypropylene dispensing tips. Out of the 40 samples, the odd numbers were used for the calibration set, and the even numbers were used as the validation set. Suitable wavelengths used for IL calibration are from about 700 nm to about 1100 nm.

Turbidity is measured in terms of equivalent IL concentration.

Equation 16 (obtained using disposable polypropylene dispensing tips)

ln(g/L IL)=1.867(A700)−0.447(A700)$^2$+0.041(A700)$^3$−1.33 where (A) is the raw absorbance measurement at the wavelength specified in nanometers.

Equation 17 (obtained using 12 mm disposable polypropylene tubes)

g/L IL=2.72(A872)−3.88(A872)$^2$+1.70(A872)$^3$+0.19 where (A) is the raw absorbance measurement at the wavelength specified in nanometers.

The following examples of primary calibrations algorithms for IL are described in U.S. Pat. No. 6,268,910 B1, U.S. Pat. No. 5,846,492 and WO 97/47972.

Equation 18 (obtained using blood bag tubing)

g/L IL=432.42(1st D A988)+40.40(1st D A1038)+0.04 where (1st D A) is the first derivative of the absorbance measurement at the wavelength specified in nanometers.

Equation 19 (obtained using blood bag tubing)

g/L IL=305.78(1st D A874)+1.12 where (1st D A) is the first derivative of the absorbance measurement at the wavelength specified in nanometers.

Equation 20 (obtained using disposable plastic dispensing tips)

g/L IL=252.16(1st D A874 nm)+0.24 where (1 st D A) is the first derivative of the absorbance measurement at the wavelength specified.

Equation 21 (obtained using translucent pipette tips)

g/L IL=296.01(A900)−0.04 where (A) is the raw absorbance measurement at the wavelength specified in nanometers.

Example 6

Calibration Algorithms for Met-Hemoglobin

Twenty nine samples comprising fresh hemolysate that contained about 95% Oxy-Hb, Met-Hb, MB, BV and IL were used to calibrate an apparatus that used TEFLON™ sample holders. BR was not added to the samples because BR does not absorb light at the wavelengths used to calibrate for either Met-Hb or MB. The Met-Hb was obtained in lyophilized form from Sigma, and was reconstituted in phosphate buffered saline. As mentioned above, the primary calibrations described herein is exemplary of the work involved in developing primary calibration algorithms.

Equation 22 (obtained using TEFLON™ sample holders)

g/L Met-Hb=69.88(1st D A645)+53.15(1st D A669)−1.17 where (1st D A) is the first derivative of the absorbance measurement at the wavelength specified.

Example 7

Calibration Algorithm for Methylene Blue

Equation 23 (obtained using TEFLON™ sample holders)

mg/L MB=162.53(1st D A702)−112.58(1st D A759)−1.17 where (1st D A) is the first derivative of the absorbance measurement at the wavelength specified.

The following example of a primary calibration algorithm for MB is described in U.S. Pat. No. 6,268,910 B1.

Equation 24 (obtained using blood bag tubing)

mg/L MB=56.04(1st D A677)+267.21(1st D A953)+4.49 where (1st D A) is the first derivative of the absorbance measurement at the wavelength specified in nanometers.

The primary calibration algorithms referred to herein are non-limiting examples obtained by a process of step-wise multiple linear regression. A primary calibration algorithm may be developed using an order derivative of absorbance of calibration samples, at one or more than one wavelength of a standard set of wavelengths, and a statistical technique selected from the group consisting of simple linear regression, multiple linear regression, and multivariate analysis, wherein the multivariate analysis is selected from the group consisting of partial least squares, principal component analysis, neural network, and genetic algorithm. It should be understood that any order derivative of absorbance can be used, for example as shown for IL (Example 5, equations 18-20). The robustness of a primary calibration algorithm depends on the inclusion of substances in the primary calibration sets that absorb or scatter light around the principal calibration wavelength(s). Furthermore, similar calibration algorithms for Total-Hb and Met-Hb can be developed for Total-Hb and Met-Hb in whole blood, using similar methods as described above, for developing the calibration algorithms in plasma.

A primary calibration algorithm can also be obtained as follows: Absorbance spectra are obtained for several samples (the primary calibration set) that cover a concentration range of a given analyte for which the primary calibration algorithm is being developed. It is preferred that the samples of the primary calibration set include all the absorbance variability expected in a sample, whereby the sample variability becomes built into the primary calibration algorithm. A multiple linear regression is then performed to develop a linear combination having the order derivative of absorbance at specific wavelengths as the independent variable, and the concentration of the analyte as the dependent variable. Other statistical methods, for example simple linear regression that uses only one wavelength, partial least squares (PLS), principal component analysis (PCA), neural network, and genetic algorithm may also be used. The equation thus obtained is a primary calibration algorithm.

In the case of Total-Hb, the independent variable, Total-Hb, should be measured by a method that measures the Total-Hb accurately (i.e., all the Hb species are accounted for), and the primary calibration set preferably contains a range of Hb concentrations, from zero g/L to the upper limit of the analytical range or dynamic range, for example from about 0% to about 100% of the Total-Hb, or any amount therebetween. Additionally, the Hb in the samples preferably comprises all the Hb species, as well as interfering substances, for example, which should not be considered limiting in any way, bilirubin, biliverdin, and methylene blue, in the primary calibration set. It is not required that every sample in the primary calibration set contain all the Hb species, or all the interfering substances. The range of values for each Hb species can be from 0% to 100% of the Total-Hb. In one aspect of the invention, a single primary calibration algorithm can be developed for Total-Hb, by using a primary calibration set just described.

In another aspect of the invention, the samples of the primary calibration set just described, are exposed to atmospheric oxygen, whereby the Deoxy-Hb changes to Oxy-Hb, and eliminates most the Deoxy-Hb species. Under these conditions, the percent Oxy-Hb and the percent "Oxy-Hb plus Deoxy-Hb" are approximately equal, and the terms Oxy-Hb and "Oxy-Hb plus Deoxy-Hb," refer to the same Hb-species. Therefore, a primary calibration algorithm can be developed for Oxy-Hb or "Oxy-Hb plus Deoxy-Hb".

Although the samples of the primary calibration set are preferably natural, (i.e., un-tampered), some analytes may need to be added in order to obtain the required concentration range. In the case of Hb species, it may be difficult to obtain samples with high concentrations of Met-Hb, Carboxy-Hb, and Sulf-Hb. When elevated levels of one or more of Met-Hb, Carboxy-Hb, and Sulf-Hb are required, chemical treatments of the samples can be used, for example, which should not be considered limiting in any way:

treatment with sodium nitrite to convert Hb into Met-Hb;
treatment with carbon monoxide to convert Hb into Carboxy-Hb; and
treatment with hydrogen sulfide to convert Hb into Sulf-Hb.

After one or more treatments as described above, one or more of Total-Hb, Oxy-Hb, Deoxy-Hb, Met-Hb, Carboxy-Hb, and Sulf-Hb may be measured on a CO-oximeter (for example, which should not be considered limiting in any way, the AVL OMNI from Roche Diagnostics). Samples, before and after treatment, preferably from the same donor, can be mixed in appropriate proportions, to obtain the required concentration ranges of the analytes.

The samples (calibration set) may also be spiked with various amounts of one or more interferents, for example, which should not be considered limiting in any way, bilirubin, biliverdin, and methylene blue. The addition of interferents provides for the development of more robust primary calibration algorithms. The primary calibration set may also be exposed to atmospheric oxygen in order to minimize the concentration of Deoxy-Hb. This would be desired if future samples to be used for prediction of unknown analyte values are also to be exposed to atmospheric oxygen.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of measuring Tot-Hb in a sample, comprising,
   i) collecting an absorbance measurement of the sample using one or more than one first or second spectroscopic apparatus comprising a first primary calibration algorithm for one of Oxy-Hb, "Oxy-Hb plus Deoxy-Hb", or "Total-Hb minus Met-Hb", and one or more than one second primary calibration algorithm for one or more than one of Met-Hb, Carboxy-Hb, or Sulf-Hb, or comprising a third primary calibration algorithm obtained by adding terms of the first primary calibration algorithm and the terms of the one or more than one second primary calibration algorithm together; and
   ii) predicting either:
      a) a first value for one of Oxy-Hb, "Oxy-Hb plus Deoxy-Hb," or "Total-Hb minus MebHb", in the sample by applying the first primary calibration algorithm to an order derivative of absorbance of the sample at one or more than one wavelength of a standard set of wavelengths, and predicting one or more than one second value for one or more than one of Met-Hb, Carboxy-Hb, or Sulf-Hb in the sample by applying the second primary calibration algorithm to an order derivative of absorbance at one or more than one wavelength of a standard set of wavelengths, and adding the first value and the one or more than one second value together to provide a measurement of Total-Hb; or
      b) Total-Hb using the third primary calibration algorithm applied to an order derivative of absorbance of the sample at one or more than one wavelength of a standard set of wavelengths.

2. The method of claim 1 wherein in the step of collecting (step i)), the first primary calibration algorithm and the one or more than one second primary calibration algorithm are generated using an order derivative of absorbance at one or more than one wavelength of a standard set of wavelengths, obtained from one or more than one first apparatus using one or more than one primary calibration set having known reference values for one or more than one of Oxy-Hb, "Oxy-Hb plus Deoxy-Hb", "Total-Hb minus Met-Hb", Met-Hb, Carboxy-Hb, or Sulf-Hb, the first primary calibration algorithm is generated for one of Oxy-Hb, "Oxy-Hb plus Deoxy-Hb," or "Total-Hb minus Met-Hb", using an order derivative of absorbance at the one or more than one wavelength of a standard set of wavelengths, the known reference values, and a statistical technique and the one or more than one second primary calibration algorithm is generated for one or more than one of Met-Hb, Carboxy-Hb, or Sulf-Hb, using an order derivative of absorbance at the one or more than one wavelength of a standard set of wavelengths, the known reference values, and the statistical technique.

3. The method of claim 2, wherein the first primary calibration algorithm and the one or more than one second primary calibration algorithm are upgraded, using a small set of unique calibrator materials that are distinct from the one or more than one primary calibration set.

4. The method of claim 2, wherein:
 i) concentration of the Oxy-Hb, the "Oxy-Hb plus Deoxy-Hb", and the "Total-Hb minus Met-Hb", are considered to be equivalent if the concentration of Oxy-Hb accounts for about 95% of the concentration of "Oxy-Hb plus Deoxy-Hb", or about 95% of the concentration of "Total-Hb minus Met-Hb", in the sample; or
 ii) concentration of the Oxy-Hb, the "Oxy-Hb plus Deoxy-Hb", and the "Total-Hb minus Met-Hb", are considered to be equivalent if the concentration of "Oxy-Hb plus Deoxy-Hb," or the concentration of "Total-Hb minus Met-Hb", in the sample, comprises about 95% Oxy-Hb.

5. The method of claim 2, wherein the standard set of wavelengths is selected from the range from about 300 nm to about 2500 nm.

6. The method of claim 2, wherein samples of the one or more than one calibration set comprises from 0% to 100% or any value therebetween, of one or more than one of Oxy-Hb, "Oxy-Hb plus Deoxy-Hb", "Total-Hb minus Met-Hb", Carboxy-Hb, Met-Hb, and Sulf-Hb.

7. The method of claim 2, wherein the statistical technique is selected from the group consisting of simple linear regression, multiple linear regression, and multivariate analysis.

8. The method of claim 7, wherein the multivariate analysis is selected from the group consisting of partial least squares, principal component analysis, neural network, and genetic algorithm.

9. The method of claim 1, wherein the first primary calibration algorithm and the one or more than one second primary calibration algorithm, or the third primary calibration algorithm, are installed on, and in operative association with, a second apparatus, and in the step of collecting (step i)), the absorbance of the sample is measured on the second apparatus to produce an absorbance measurement.

10. The method of claim 1, wherein the one or more than one apparatus is a second apparatus, and wherein a step of data pre-processing follows the step of collecting (step i) and precedes the step of predicting (Step ii).

11. The method of claim 10, wherein the step of data pre-processing includes a process selected from the group consisting of: calculation of interpolated absorbances; smoothing of absorbances; calculation of a first and higher order derivative of absorbance; multiplicative scatter correction; data transformation;
 photometric correction, and a combination thereof.

12. The method of claim 1, wherein the sample is one of whole blood, serum, plasma, urine, synovial fluid, lymphatic fluid, sputum, feces, or cerebrospinal fluid.

13. The method of claim 12, wherein the Total-Hb, is used as an indicator of hemolysis.

14. The method of claim 1, wherein the sample is exposed to atmospheric oxygen prior to the absorbance measurement.

15. The method of claim 1, wherein the Total-Hb is a combination of endogenous Hb and exogenous Hb, and wherein the exogenous Hb is one or more than one Hb-based blood substitute, and wherein the Met-Hb is a combination of endogenous Met-Hb and the Met-Hb form of the one or more than one Hb-based blood substitute.

16. The method of claim 1, wherein by measuring the proportion of Total-Hb that is in the form of Met-Hb, provides a method of monitoring degradation or reversal of degradation of one or more than one Hb-based blood substitute in the sample.

17. A reagentless spectroscopic method for measuring Total-Hb in a sample comprising:
 i) collecting an absorbance measurement of the sample using one or more than one spectroscopic apparatus comprising a primary calibration algorithm for Total-Hb, the sample having been exposed to atmospheric oxygen; and
 ii) predicting a value for Total-Hb in the sample by applying the primary calibration algorithm to an order derivative of absorbance of the sample at one or more than one wavelength of a standard set of wavelengths, to provide a measurement of Total-Hb,
 wherein in the step of collecting (step i)), the primary calibration algorithm for Total-Hb is generated using an order derivative of absorbance at one or more than one wavelength of a standard set of wavelengths obtained from one or more than one first apparatus, known reference values obtained from a primary calibration set, and a statistical technique, wherein each sample of the calibration set is exposed to atmospheric oxygen before spectroscopic measurement, and wherein the calibration set comprises known reference values from about 0 to about 100% or any value therebetween, of one or more than one of Oxy-Hb, Deoxy-Hb. Met-Hb, Carboxy-Hb, and Sulf-Hb, and
 wherein the first primary calibration algorithm is upgraded using a small set of unique calibrator materials that are distinct from the primary calibration set prior to obtaining the absorbance measurement.

18. The method of claim 17, wherein the primary calibration algorithm is installed on, and is in operative association with, a second apparatus, and in the step of collecting (step i)), the absorbance of the sample is measured on the second apparatus to produce an absorbance measurement.

19. The method of claim 17, wherein a step of data pre-processing follows the step of collecting (step i)), and before the step of predicting (step (ii)).

20. The method of claim 19, wherein the step of data pre-processing includes a process selected from the group consisting of: calculation of interpolated absorbances; smoothing of absorbances; calculation of a first and higher order derivative of absorbance; multiplicative scatter correction; data transformation; photometric correction, and a combination thereof.

21. The method of claim 17, wherein the standard set of wavelengths is selected from the range from about 300 nm to about 2500 nm, or any amount therebetween.

22. The method of claim 17, wherein the statistical technique is selected from the group consisting of simple linear regression, multiple linear regression, and multivariate analysis.

23. The method of claim 22, wherein the multivariate analysis is selected from the group consisting of partial least squares, principal component analysis, neural network, and genetic algorithm.

24. The method of claim 17, wherein the sample is one of whole blood, serum, plasma, urine, synovial fluid, lymphatic fluid, sputum, feces, or cerebrospinal fluid.

25. The method of claim 24, wherein the Total-Hb, is used as an indicator of hemolysis.

26. The method of claim 17, wherein the Total-Hb is a combination of endogenous Hb and exogenous Hb, and wherein the exogenous Hb is one or more than one Hb-based blood substitute.

27. A spectroscopic apparatus, comprising:
- a) a source of electromagnetic radiation (EMR);
- b) a first aperture located between the source of EMR and a sample slot to produce a light path therebetween;
- c) the sample slot in the apparatus for receiving a sample vessel to be placed within the light path;
- d) a second aperture located in the light path, between the sample slot and one or more than one photodetector, the one or more than one photodetector in operative association with the spectroscopic apparatus; and either
- e) a first primary calibration algorithm in operative association with the spectroscopic apparatus, the first primary calibration algorithm generated for one of Oxy-Hb, "Oxy-Hb plus Deoxy-Hb," or "Total-Hb minus Met-Hb", using an order derivative of absorbance at one or more than one wavelength of a standard set of wavelengths obtained from one or more than one first apparatus using one or more than one calibration set having known reference values for one or more than one of Oxy-Hb, "Oxy-Hb plus Deoxy-Hb", "Total-Hb minus Met-Hb", Met-Hb, Carboxy-Hb, or Sulf-Hb, and a statistical technique, and one or more than one second primary calibration algorithm in operative association with the spectroscopic apparatus, the one or more than one second primary calibration algorithm generated for one or more than one of MetHb, Carboxy-Hb, or Sulf-Hb, using an order derivative of absorbance at the one or more than one wavelength of a standard set of wavelengths, the known reference values, and the statistical technique; or
- f) a third primary calibration algorithm in operative association with the spectroscopic apparatus, the third primary calibration algorithm obtained by adding the terms of the first primary calibration algorithm and the terms of the one or more than one second primary calibration algorithm together.

* * * * *